(12) United States Patent
Cobb

(10) Patent No.: US 9,506,115 B2
(45) Date of Patent: **\*Nov. 29, 2016**

(54) MUTATIONAL ANALYSIS OF JAK2

(71) Applicant: Epistem Limited, Manchester (GB)

(72) Inventor: Ben Cobb, Wiltshire (GB)

(73) Assignee: Epistem Limited, Manchester (GB)

( * ) Notice: Subject to any disclaimer, the term of this patent is extended or adjusted under 35 U.S.C. 154(b) by 0 days.

This patent is subject to a terminal disclaimer.

(21) Appl. No.: 14/348,508

(22) PCT Filed: Sep. 25, 2012

(86) PCT No.: PCT/GB2012/052366
§ 371 (c)(1),
(2) Date: Mar. 28, 2014

(87) PCT Pub. No.: WO2013/045908
PCT Pub. Date: Apr. 4, 2013

(65) Prior Publication Data
US 2014/0255937 A1    Sep. 11, 2014

(30) Foreign Application Priority Data
Sep. 30, 2011 (GB) .................. 1116876.2

(51) Int. Cl.
*C07H 21/04* (2006.01)
*C12Q 1/68* (2006.01)

(52) U.S. Cl.
CPC .......... *C12Q 1/6883* (2013.01); *C12Q 1/6858* (2013.01); *C12Q 2600/156* (2013.01)

(58) Field of Classification Search
None
See application file for complete search history.

(56) References Cited

U.S. PATENT DOCUMENTS

| | | | | |
|---|---|---|---|---|
| 8,354,523 B2 * | 1/2013 | Mao | ............................... | 435/6.1 |
| 9,005,932 B2 * | 4/2015 | Cobb | .................. | C12Q 1/6858 435/6.1 |
| 2007/0224598 A1 * | 9/2007 | Chang | .................. | C12Q 1/6883 435/6.12 |
| 2008/0076135 A1 | 3/2008 | Vainchenker et al. | | |
| 2008/0176226 A1 | 7/2008 | Chiou et al. | | |
| 2009/0123920 A1 | 5/2009 | Albitar | | |
| 2010/0068713 A1 | 3/2010 | Hirai et al. | | |
| 2010/0173311 A1 | 7/2010 | Grow et al. | | |

FOREIGN PATENT DOCUMENTS

| | | |
|---|---|---|
| EP | 2119796 A1 | 11/2009 |
| WO | WO-2006/045827 A1 | 5/2006 |
| WO | WO-2007/106899 A2 | 9/2007 |
| WO | WO-2010/054254 A1 | 5/2010 |

OTHER PUBLICATIONS

Hammond et al. (J. Molecular Diagnosis, vol. 9, No. 2, pp. 242-248, Apr. 2007).*
Combined Search and Examination Report for GB/1116876.2, 18 pages, (Jan. 27, 2012).
French, D.J. et al., Ultra-rapid DNA analysis using HyBeaconTM probes and direct PCR amplification from saliva, Molecular and Cellular Probes,16(5):319-326 (2002).
International Search Report for PCT/GB2012/052366, 6 pages, (Dec. 11, 2012).
Laughlin, T.S., et al., Detection of Exon 12 Mutations in the JAK2 Gene Enhanced Analytical Sensitivity Using Clamped PCR and Nucleotide Sequencing, Journal of Molecular Diagnostics, l2(3):278-282 (2010).
Scott, L.M., et al, JAK2 Exon 12 Mutations in Polycythemia Vera and Idiopathic Erythrocytosis, The New England Journal of Medicine, 356(5):459-468 (2007).
Wu, Z., et al., Development and Inter-Laboratory Validation of Unlabeled Probe Melting Curve Analysis for Detection of JAK2 V617F Mutation in Polycythemia Vera, PLoS One, 6(10):1-7 (2011).
Written Opinion for PCT/GB2012/052366, 6 pages, (Dec. 11, 2012).

* cited by examiner

*Primary Examiner* — Jeanine A Goldberg
(74) *Attorney, Agent, or Firm* — Choate, Hall & Stewart LLP; Brenda Herschbach Jarrell; Michael L. Vetter

(57) ABSTRACT

An assay for mutations in JAK2 is described. The assay uses selective amplification of mutant alleles with a blocker probe which preferentially hybridizes to wild type alleles. The same probe is then used to detect presence or absence of wild type sequences. It is not necessary to know the specific mutant sequence beforehand.

13 Claims, 18 Drawing Sheets

Fig 1

```
   1 ctgcaggaag gagagaggaa gaggagcaga aggggcagc agcggacgcc gctaacggcc
  61 tccctcggcg ctgacaggct gggccggcgc ccggctcgct tgggtgttcg cgtcgccact
 121 tcggcttctc ggccggtcgg gcccctcggc ccgggcttgc ggcgcgcgtc ggggctgagg
 181 gctgctgcgg cgcagggaga ggcctggtcc tcgctgccga gggatgtgag tgggagctga
 241 gcccacactg gagggccccc gagggcccag cctggaggtc gttcagagcc gtgcccgtcc
 301 cggggcttcg cagaccttga cccgccgggt aggagccgcc cctgcgggct cgagggcgcg
 361 ctctggtcgc ccgatctgtg tagccggttt cagaagcagg caacaggaac aagatgtgaa
 421 ctgtttctct tctgcagaaa aagaggctct tcctcctcct cccgcgacgg caaatgttct
 481 gaaaaagact ctgcatggga atggcctgcc ttacgatgac agaaatggag ggaacatcca
 541 cctcttctat atatcagaat ggtgatattt ctggaaatgc caattctatg aagcaaatag
 601 atccagttct tcaggtgtat ctttaccatt cccttgggaa atctgaggca gattatctga
 661 cctttccatc tggggagtat gttgcagaag aaatctgtat tgctgcttct aaagcttgtg
 721 gtatcacacc tgtgtatcat aatatgtttg ctttaatgag tgaaacagaa aggatctggt
 781 atccacccaa ccatgtcttc catatagatg agtcaaccag gcataatgta ctctacagaa
 841 taagatttta ctttcctcgt tggtattgca gtggcagcaa cagagcctat cggcatggaa
 901 tatctcgagg tgctgaagct cctcttcttg atgactttgt catgtcttac ctctttgctc
 961 agtggcggca tgattttgtg cacggatgga taaaagtacc tgtgactcat gaaacacagg
1021 aagaatgtct tgggatggca gtgttagata tgatgagaat agccaaagaa aacgatcaaa
1081 ccccactggc catctataac tctatcagct acaagacatt cttaccaaaa tgtattcgag
1141 caaagatcca agactatcat attttgacaa ggaagcgaat aaggtacaga tttcgcagat
1201 ttattcagca attcagccaa tgcaaagcca ctgccagaaa cttgaaactt aagtatctta
1261 taaatctgga aactctgcag tctgccttct acacagagaa atttgaagta aagaacctg
1321 gaagtggtcc ttcaggtgag gagattttg caaccattat aataactgga aacggtggaa
1381 ttcagtggtc aagagggaaa cataaagaaa gtgagacact gacagaacag gatttacagt
1441 tatattgcga ttttcctaat attattgatg tcagtattaa gcaagcaaac caagagggtt
1501 caaatgaaag ccgagttgta actatccata agcaagatgg taaaaatctg gaaattgaac
1561 ttagctcatt aagggaagct ttgtctttcg tgtcattaat tgatggatat tatagattaa
1621 ctgcagatgc acatcattac ctctgtaaag aagtagcacc tccagccgtg cttgaaaata
1681 tacaaagcaa ctgtcatggc ccaatttcga tggattttgc cattagtaaa ctgaagaaag
1741 caggtaatca gactggactg tatgtacttc gatgcagtcc taaggacttt aataaatatt
```

Fig 1 continued

```
1801 ttttgactttt tgctgtcgag cgagaaaatg tcattgaata taaacactgt ttgattacaa
1861 aaaatgagaa tgaagagtac aacctcagtg ggacaaagaa gaacttcagc agtcttaaag
1921 atcttttgaa ttgttaccag atggaaactg ttcgctcaga caatataatt ttccagttta
1981 ctaaatgctg tcccccaaag ccaaaagata aatcaaacct tctagtcttc agaacgaatg
2041 gtgtttctga tgtaccaacc tcaccaacat tacagaggcc tactcatatg aaccaaatgg
2101 tgtttcacaa aatcagaaat gaagatttga tatttaatga aagccttggc caaggcactt
2161 ttacaaagat ttttaaaggc gtacgaagag aagtaggaga ctacggtcaa ctgcatgaaa
2221 cagaagttct tttaaaagtt ctggataaag cacacagaaa ctattcagag tctttctttg
2281 aagcagcaag tatgatgagc aagctttctc acaagcattt ggttttaaat tatggagtat
2341 gtgtctgtgg agacgagaat attctggttc aggagtttgt aaaatttgga tcactagata
2401 catatctgaa aaagaataaa aattgtataa atatattatg gaaacttgaa gttgctaaac
2461 agttggcatg ggccatgcat tttctagaag aaaacaccct tattcatggg aatgtatgtg
2521 ccaaaaatat tctgcttatc agagaagaag acaggaagac aggaaatcct cctttcatca
2581 aacttagtga tcctggcatt agtattacag ttttgccaaa ggacattctt caggagagaa
2641 taccatgggt accacctgaa tgcattgaaa atcctaaaaa tttaaatttg gcaacagaca
2701 aatggagttt tggtaccact ttgtgggaaa tctgcagtgg aggagataaa cctctaagtg
2761 ctctggattc tcaaagaaag ctacaatttt atgaagatag gcatcagctt cctgcaccaa
2821 agtgggcaga attagcaaac cttataaata attgtatgga ttatgaacca gatttcaggc
2881 cttctttcag agccatcata cgagatctta acagtttgtt tactccagat tatgaactat
2941 taacagaaaa tgacatgtta ccaaatatga ggataggtgc cctggggttt tctggtgcct
3001 ttgaagaccg ggatcctaca cagtttgaag agagacattt gaaatttcta cagcaacttg
3061 gcaagggtaa ttttgggagt gtggagatgt gccggtatga ccctctacag gacaacactg
3121 gggaggtggt cgctgtaaaa aagcttcagc atagtactga agagcaccta agagactttg
3181 aaagggaaat tgaaatcctg aatcccatac agcatgacaa cattgtaaag tacaagggag
3241 tgtgctacag tgctggtcgg cgtaatctaa aattaattat ggaatattta ccatatggaa
3301 gtttacgaga ctatcttcaa aaacataaag aacggataga tcacataaaa cttctgcagt
3361 acacatctca gatatgcaag ggtatggagt atcttggtac aaaaaggtat atccacaggg
3421 atctggcaac gagaaatata ttggtggaga acgagaacag agttaaaatt ggagatttttg
3481 ggttaaccaa agtcttgcca caagacaaag aatactataa agtaaaagaa cctggtgaaa
3541 gtcccatatt ctggtatgct ccagaatcac tgacagagag caagttttct gtggcctcag
3601 atgtttggag ctttggagtg gttctgtatg aacttttcac atacattgag aagagtaaaa
```

Fig 1 continued

```
3661 gtccaccagc ggaatttatg cgtatgattg gcaatgacaa acaaggacag atgatcgtgt
3721 tccatttgat agaacttttg aagaataatg gaagattacc aagaccagat ggatgcccag
3781 atgagatcta tatgatcatg acagaatgct ggaacaataa tgtaaatcaa cgcccctcct
3841 ttagggatct agctcttcga gtggatcaaa taagggataa catggctgga tgaaagaaat
3901 gaccttcatt ctgagaccaa agtagattta cagaacaaag ttttatattt cacattgctg
3961 tggactatta ttacatatat cattattata taaatcatga tgctagccag caaagatgtg
4021 aaaatatctg ctcaaaactt tcaaagttta gtaagttttt cttcatgagg ccaccagtaa
4081 aagacattaa tgagaattcc ttagcaagga ttttgtaaga agtttcttaa acattgtcag
4141 ttaacatcac tcttgtctgg caaaagaaaa aaaatagact ttttcaactc agcttttga
4201 gacctgaaaa aattattatg taaattttgc aatgttaaag atgcacagaa tatgtatgta
4261 tagtttttac cacagtggat gtataatacc ttggcatctt gtgtgatgtt ttacacacat
4321 gagggctggt gttcattaat actgttttct aattttccca tagttaatct ataattaatt
4381 acttcactat acaaacaaat taagatgttc agataattga ataagtacct ttgtgtcctt
4441 gttcatttat atcgctggcc agcattataa gcaggtgtat acttttagct tgtagttcca
4501 tgtactgtaa atattttttca cataaaggga acaaatgtct agttttattt gtataggaaa
4561 tttccctgac cctaaataat acattttgaa atgaaacaag cttacaaaga tataatctat
4621 tttattatgg tttcccttgt atctatttgt ggtgaatgtg tttttaaat ggaactatct
4681 ccaaattttt ctaagactac tatgaacagt tttcttttaa aattttgaga ttaagaatgc
4741 caggaatatt gtcatccttt gagctgctga ctgccaataa cattcttcga tctctgggat
4801 ttatgctcat gaactaaatt taagcttaag ccataaaata gattagattg ttttttaaaa
4861 atggatagct cattaagaag tgcagcaggt taagaatttt ttcctaaaga ctgtatattt
4921 gagggtttc agaattttgc attgcagtca tagaagagat ttatttcctt tttagagggg
4981 aaatgaggta ataagtaaa aaagtatgct tgttaatttt attcaagaat gccagtagaa
5041 aattcataac gtgtatcttt aagaaaatg agcatacatc ttaaatcttt tcaattaagt
5101 ataaggggtt gttcgttgtt gtcatttgtt atagtgctac tccactttag acaccatagc
5161 taaaataaaa tatggtgggt tttgtgtgtg tgtgtgtgtg tgtgtgtgtg tgtgtgtgtg
5221 tgttatttat acaaaactta aaatacttgc tgttttgatt aaaaagaaaa tagtttctta
5281 cttta
```

Fig 2

| Amplicon Details | | | | |
|---|---|---|---|---|
| Product Length | Tm | Distance from 3'UTR | Single Exon | Structure |
| 112 | 69.6 | 318 | ND | NONE |

| Primer Details | | | | | |
|---|---|---|---|---|---|
| Sense Primer | Position | Tm | GC% | 3'dG | Dimer |
| TCTTTGAAGCAGCAAGTATGATGA | 183 | 57.7 | 37.5 | -3 | -0.8 |
| Anti-sense Primer | Position | Tm | GC% | 3'dG | Dimer |
| GCATTAGAAAGCCTGTAGTTTTACTT | 294 | 57.5 | 34.6 | -2.8 | -0.9 |

| Further information |
|---|

HyBeacon Probe Sequence: TTTAAATTATGGAGTATGTGTCTGTGGAGA

Fig 5

| Substitutions ||
|---|---|
| Position | Mutation(n) |
| 1831 | c.1831T>C(3) |
| 1832 | c.1832T>C(1) |
| 1849 | c.1849G>A(1) c.1849G>T(26418) |
| 1851 | c.1851C>T(1) |
| 1852 | c.1852T>C(4) |
| 1853 | c.1853G>T(1) |
| 1860 | c.1860C>A(2) |

| Insertions ||
|---|---|
| Position | Mutation(n) |
| No Insertions in Current Selection ||

| Deletions ||
|---|---|
| Position | Mutation(n) |
| No Deletions in Current Selection ||

| Complex ||
|---|---|
| Position | Mutation(n) |
| 1848 | c.1848_1849TG>CT(2) |
| 1849 | c.1849_1852GTCT>TTCC(1) c.1849_1852GTCT>TTTC(1) |

| Fusion Mutations ||
|---|---|
| | Mutation(n) |
| ETV6(NM_001987.3):r.? _ JAK2(ENST00000381652):r.?(1) ||
| BCR(NM_004327):r.1_3279 _ JAK2(ENST00000381652):r.1830_5097(1) ||
| BCR(NM_004327):r.1_1875 _ JAK2(ENST00000381652):r.2929_5097(1) ||
| BCR(NM_004327):r.1_1875 _ JAK2(ENST00000381652):r.2626_5097(1) ||
| ETV6(NM_001987.3):r.1_1283 _ JAK2(ENST00000381652):r.2929_5097(1) ||
| JAK2(ENST00000381652):r.1_2928 _ ETV6(NM_001987.3):r.1284_5992(1) ||
| JAK2(ENST00000381652):r.1_1820 _ PCM1(ENST00000325083):r.8264_8779(2) ||
| PCM1(ENST00000325083):r.1_6263 _ JAK2(ENST00000381652):r.1821_5097(4) ||
| PCM1(ENST00000325083):r.? _ JAK2(ENST00000381652):r.?(6) ||
| PCM1(ENST00000325083):r.1_4365 _ JAK2(ENST00000381652):r.2058_5097(1) ||
| PCM1(ENST00000325083):r.1_4530 _ JAK2(ENST00000381652):r.2929_5097(1) ||
| JAK2(ENST00000381652):r.1_2007 _ PCM1(ENST00000325083):r.4531_8779(1) ||
| PCM1(ENST00000325083):r.1_4832 _ JAK2(ENST00000381652):r.1551_5097(1) ||
| PCM1(ENST00000325083):r.1_6263 _ JAK2(ENST00000381652):r.1551_5097(1) ||
| PCM1(ENST00000325083):r.1_6263+5205 _ JAK2(ENST00000381652):r.1845_5097(1) ||
| SSBP2(ENST00000326872):r.1_583 _ JAK2(ENST00000381652):r.1821_5097(1) ||
| ETV6(NM_001987.3):r.1_737+8854 _ JAK2(ENST00000381652):r.2487-499_5097(1) ||
| ETV6(NM_001987.3):r.1_1283+5216_ins3600 _ JAK2(ENST00000381652):r.1887_5097(1) ||
| SEC31A(NM_0018211):r.1_3012 _ JAK2(ENST00000381652):r.2626_5097(2) ||
| PAX5(NM_016734.1):r.1_1052 _ JAK2(ENST00000381652):r.2929_5097(3) ||
| JAK2(ENST00000381652):r.1_2928 _ PAX5(NM_016734.1):r.1053_3650(3) ||

| Other Mutations ||
|---|---|
| Position | Mutation(n) |
| No Other Mutations in Current Selection ||

Fig 6

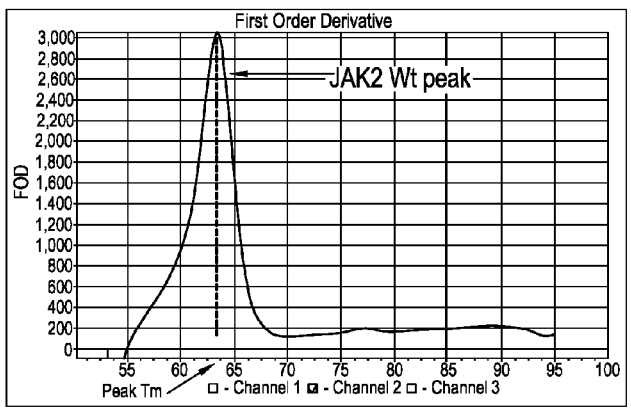

Example #1: Melt Curve profile of sample containing 100% Wild-type (Wt) JAK2

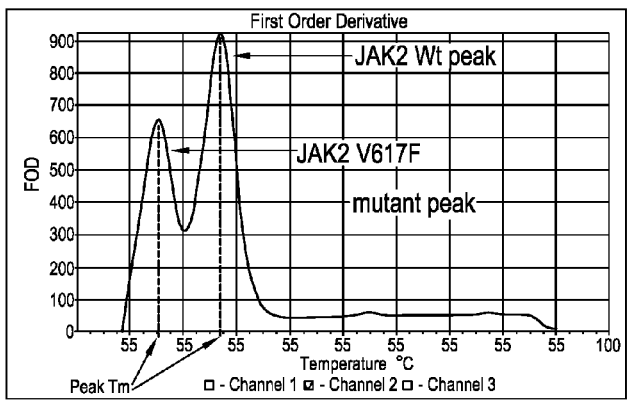

Example #2: Melt Curve profile of mixed sample containing JAK2 Wild-type (Wt)

Fig 7

| Step Index | Temperatuure | Dwell | Repeat | Phase | Phase Step | Tag | Type |
|---|---|---|---|---|---|---|---|
| 1 | 95 | 300 | 0 | 1 | 1 | 1 | Isothermal |
| 2 | 50 | 5 | 0 | 2 | 1 | 8 | Calibration 2 |
| 3 | 95 | 5 | 0 | 2 | 2 | 7 | Calibration 1 |
| 4 | 95 | 15 | 39 | 3 | 1 | 2 | Denaturation |
| 5 | 53 | 15 | 39 | 3 | 2 | 4 | Anneal |
| 6 | 72 | 15 | 39 | 3 | 3 | 3 | Extension |
| 7 | 50 | 0 | 0 | 4 | 1 | 8 | Calibration 2 |
| 8 | 95 | 0 | 0 | 4 | 2 | 7 | Calibration 1 |
| 9 | 50 | 10 | 0 | 5 | 1 | 6 | StartMelt |
| 10 | 95 | 0 | 0 | 5 | 2 | 5 | Melt |
| 11 | 35 | 0 | 0 | 6 | 1 | 9 | Stop |

Isothermal runtime: 00:05:12  label5
Cycling runtime: 00:54:40  label5
Calibration runtime: 00:00:42  label5
Melt runtime: 00:08:07  label5

* Peak not detected by software

MUTATIONAL ANALYSIS OF JAK2

CROSS-REFERENCE TO RELATED APPLICATIONS

This application is a national phase entry of international application serial number PCT/GB2012/052366, filed Sep. 25, 2012, which claims priority to Great Britain Application No. 1116876.2, filed Sep. 30, 2011, the entire contents of which are both herein incorporated by reference.

FIELD OF THE INVENTION

The present invention relates to a method for analysing genetic mutations, and in particular single nucleotide polymorphisms (SNPs) in the JAK2 gene. Aspects of the invention also relate nucleic acid probes and primers of use in analysing such mutations.

BACKGROUND TO THE INVENTION

Janus kinase 2 (commonly called JAK2) is a human protein that has been implicated in signalling by members of the type II cytokine receptor family (e.g. interferon receptors), the GM-CSF receptor family (IL-3R, IL-5R and GM-CSF-R), the gp130 receptor family (e.g. IL-6R), and the single chain receptors (e.g. Epo-R, Tpo-R, GH-R, PRL-R). JAK2 signalling is activated downstream from the prolactin receptor. Mutations in JAK2 have been implicated in polycythemia vera, essential thrombocythemia, and other myeloproliferative disorders. This mutation, a change of valine to phenylalanine at the 617 position, appears to render hematopoietic cells more sensitive to growth factors such as erythropoietin and thrombopoietin.

Polycythemia vera (also known as erythremia, or primary polycythemia) is a blood disorder in which the bone marrow makes too many red blood cells. It may also result in the overproduction of white blood cells and platelets. Most of the health concerns associated with polycythemia vera are caused by the blood being thicker as a result of the increased red blood cells. It is more common in the elderly and may be symptomatic or asymptomatic.

It is of benefit to provide a rapid and simple test for diagnosis of polycythemia vera.

U.S. Pat. No. 7,429,456 describes the identification of the valine to phenylalanine (V617F) mutation in JAK2, and describes a test for detecting the presence of the mutation. SEQ ID NO 1 of U.S. Pat. No. 7,429,456 gives the amino acid sequence of the V617F form of human JAK2, and SEQ ID NO 2 of U.S. Pat. No. 7,429,456 gives the nucleic acid sequence encoding the amino acid sequence (the gene sequence mutation is referred to as G1849T); reference is also made to the wild type form of the protein, under NCBI accession number NM 004972. The diagnostic test described in this patent makes use of nucleic acid probes which span the mutated T nucleotide at position 1849 of the nucleic acid sequence. The presence of the mutation is detected by PCR amplification of the region flanking position 1849, followed by hybridisation with a probe including the T1849 nucleotide. If there is hybridisation, then the mutation is present. Alternatively, the PCR primers may be directed to the mutant sequence, such that the mutant form will be selectively amplified. The mRNA sequence of JAK2 (SEQ ID NO 4) is given in FIG. 1 of the present application. Position G1849 corresponds to nt 2343 of SEQ ID NO 4 of FIG. 1. Such assays are specific for the particular mutation.

It would be useful to provide an alternative diagnostic test.

Our co-pending patent application GB 1100150.0 describes a method for detecting and analysing SNPs in target genes, based on preferential amplification of the mutant sequence. The melting temperature (Tm) of double stranded DNA depends on the extent of base pair hybridisation; where there is a mismatch between a probe and a target sequence (for example, due to the presence of a SNP) then the Tm will differ compared with when there is no mismatch. The method described in GB 1100150.0 involves the use of PCR primers to flanking regions of the target sequence in combination with a blocking probe which preferentially hybridises to either the wild type or the mutant sequence. The probe is designed such that it has a lower Tm when binding to the sequence to be blocked (for example, the wild type sequence) than when binding to the sequence to be amplified (for example, the mutant sequence). Amplification is carried out at a temperature such that the probe hybridises to the sequence to be blocked but not the sequence to be amplified, and thus only the other sequence is amplified. The same probe may then be used to detect the presence of the amplified sequence, and to detect the relative ratios of the amplified to non-amplified sequence.

The present invention applies related methods to the detection of mutations in JAK2.

SUMMARY OF THE INVENTION

According to a first aspect of the present invention, there is provided a method of detecting the absence of a wild type allele of a locus in the JAK2 gene having at least first mutant and wild type alleles, the method comprising:
  a) providing a reaction mix comprising
    i) a sample including nucleic acid representing at least a portion of the JAK2 gene;
    ii) an oligonucleotide probe which hybridises to the mutant allele with a lower melting temperature (Tm) than that with which it hybridises to the wild type allele;
    iii) a pair of oligonucleotide primers for nucleic acid amplification, the primers hybridising to the nucleic acid in the sample at first and second sites flanking the oligonucleotide probe binding site; wherein the Tm of the primer:sample is higher than the Tm of the probe:mutant allele;
  b) maintaining the reaction mix at a temperature between the probe:mutant allele Tm and the probe:wild type allele Tm, such that the probe preferentially hybridises to the wild type allele;
  c) carrying out a thermal cycling amplification on the reaction mix, the amplification including a melt phase, an annealing phase, and an extension phase, in which the temperatures of the extension and annealing phases are between the probe:mutant allele Tm and the probe: wild type allele Tm, such that the probe is hybridised to the wild type allele during these phases; to thereby amplify the mutant allele; and
  d) detecting hybridisation of the probe to the sample at a temperature at or below the probe:mutant allele Tm; detecting hybridisation of the probe to the sample at a higher temperature at or below the probe:wild type allele Tm; and comparing the two; to thereby detect the presence or absence of the wild type allele.

Thus, the present invention allows a first mutant allele to be preferentially amplified compared with a second wild type allele. The same probe as acted as the blocking probe during amplification can be used in the detection phase. This simplifies the procedure significantly. A key feature of this invention is that the probe used detects the presence or absence of the wild type allele; that is, if the wild type allele is present, it is detected, whereas if it is absent, it is not detected. Any mutant sequence will be preferentially amplified, so reducing the relative copy number of the wild type sequence even if the mutant is relatively rare (for example, only present in a few cells in the sample). Where the mutant is present, wild type detection will be reduced compared to mutant detection at the lower temperature. The method is not tied to the detection of any specific mutant allele, and is therefore more flexible than alternative methods which rely on the use of a probe specific for one mutant allele.

The extension and annealing phases may be combined, in that they may be carried out at the same temperature.

Preferably the portion of the JAK2 gene represented by the sample in step a)i) spans nt 2343 of the JAK2 gene (nt 2343 as defined by reference to SEQ ID NO 4 given in FIG. 1). The mutant allele is preferably a mutation in nt2343. In a preferred embodiment, the mutant form is T2343, while the wild type is G2343. This corresponds to the V617F mutation.

However, the invention is not limited to use with the V617F mutation. For example, the probe may be designed to span nt 2343 and sufficient additional nucleotides to be able to have a differential Tm with respect to mutations in amino acid residue 618, for example the rare C618F mutation. This corresponds to a nucleotide substitution G2347T. Since the invention relies on the differential Tm between the probe binding to the wild type sequence and binding to the mutant sequence, the identity of the mutant sequence is not significant.

In preferred embodiments, the probe spans nt 2343. The probe preferably includes a nucleotide corresponding to the wild type residue G2343; any mismatch to this will result in a lower Tm.

The oligonucleotide probe is preferably at least 15, 20, 25, 26, 27, 28, 29, 30 nucleotides in length.

A particularly preferred oligonucleotide probe comprises, or consists of, the sequence TTT AAA TTA TGG AGT ATG TGT CTG TGG AGA (SEQ ID NO: 1). This corresponds to nt 2324 to 2353 of the JAK2 sequence given in FIG. 1 (probe binding region is underlined).

The primers preferably amplify a portion of the JAK2 sequence which is at least 50, 60, 70, 80, 90, 100 nucleotides in length. Preferred primers include TCT TTG AAG CAG CAA GTA TGA TGA (SEQ ID NO 2; sense primer) and GCA TTA GAA AGC CTG TAG TTT TAC TT (SEQ ID NO 3, antisense primer). These provide an amplicon of 112 nt in length.

The temperatures of the extension and annealing phases may be the same (in which case a combined extension-annealing phase may be used), but are preferably different. The temperature of the melt phase may be higher than the temperatures of the Tm primer:sample and the Tm probe:wild type allele. However, this is not essential; for example, the Tm primer:sample may be lower than the Tm probe:wild type allele, in which case the melt phase may be at a temperature between these two values, such that effectively the probe remains hybridised to the wild type allele throughout the amplification reaction.

During the extension phase, the oligonucleotide probe remains hybridised to the wild type allele. This prevents strand extension of the primer hybridised to the same nucleic acid, whereas primers hybridised to the mutant allele are free to undergo strand extension since the probe is not hybridised to that allele. In this way, the mutant allele will be preferentially amplified. As noted below, in certain embodiments one or both of the primers may overlap with the probe binding site such that the probe competes with the primer for binding; this can prevent binding of the primer and hence strand extension. In other (preferred) embodiments the primers and probe do not overlap, but the primer prevents further strand extension.

The locus may be a multi-allelic locus; that is, there are more than two alleles possible at that locus. In such a situation, one allele may be designated the wild type allele, and the others are mutant alleles. The probe is preferably selected such that the Tm probe:wild type allele is higher than any of the Tm probe:mutant allele. The method may be used to preferentially amplify any of the mutant alleles which are present. This is of particular benefit when the method is used to investigate somatic mutations, where there may be several different mutations present in different cell lines. In preferred embodiments, the Tm of each possible probe:allele combination differs. Preferably the Tm differs by at least 0.25 C degree, more preferably at least 0.5 C degree, most preferably at least 0.75 C degree. This allows for fine discrimination to be made between each allele. For example, if there are four alleles, and only two are to be amplified, then the extension temperature may be set at an appropriate level such that the probe hybridises to the other two of the alleles.

The probe is preferably substantially, and more preferably fully, complementary to one strand of the target allele. The probe may be fully complementary to one strand of the wild type allele. The mutant allele may differ from the sequence of the second allele by one or more point mutations (single nucleotide polymorphisms, SNPs). It is possible that the mutant allele includes more than one SNP, for example at different codons. It is one of the advantages of the present method that it is possible to preferentially amplify mutant alleles potentially including more than one SNP. Alternatively, the mutant allele may differ from the sequence of the wild type allele by one or more deletions.

Preferably the probe is DNA.

The differences in sequence between the mutant and wild type alleles are preferably internal to the region where the probe binds; that is, any mismatches between the probe and the mutant allele are not at the ends of the probe.

The probe may be labelled. For example, the probe may include a fluorescent or a radioactive label, or may be labelled with a ligand to which a secondary probe may bind. Preferably the probe is labelled with a fluorescent label, and preferably also the label generates a differential signal depending on whether the probe has hybridised to a target strand (that is, the probe is part of a double stranded nucleic acid) or not (the probe is single stranded). A preferred probe is a HyBeacon® probe (see, for example, Mol Cell Probes. 2002 October; 16(5):319-26, "Ultra-rapid DNA analysis using HyBeacon probes and direct PCR amplification from saliva", French D J, Archard C L, Andersen M T, McDowell D G). Generation of differential signals allows easy and rapid analysis of whether the probe has bound to a target.

The step of detecting hybridised probe molecules may further comprise quantification of the relative amounts of mutant and wild type alleles in the amplification mix. In certain embodiments of the invention, a detection step may be carried out before as well as after the amplification step. In a preferred embodiment, the ratio of mutant to wild type alleles may be measured by: maintaining the reaction mix at a first temperature at or below the Tm of the probe:mutant allele; detecting hybridised probe molecules; increasing the reaction mix to a second temperature above the Tm of the probe:mutant allele but at or below the Tm of the probe:wild type allele; and detecting hybridised probe molecules. At the first, lower temperature, probe will be hybridised to both mutant and wild type alleles, while at the second higher temperature, probe will be hybridised only to the wild type allele.

Where the locus is multi-allelic, then the detection step may further comprise raising the reaction mix to one or more intermediate temperatures, and detecting hybridised probe molecules at each intermediate temperature. This is particularly preferred when each probe:allele combination has a distinct Tm. This embodiment of the invention allows both amplification and quantification of multiple distinct mutant alleles in a single experiment.

The primers preferably bind at a region outside the region where the probe binds; that is, a first primer binds 3'-wards of the probe target, while a second primer binds 5'-wards of the probe target (bearing in mind that the primers will bind to different strands of the duplex DNA). When the primers undergo strand extension, this is blocked by the bound probe, such that the strand cannot be amplified. In certain embodiments the primers may bind adjacent to the region where the probe binds, or may even overlap with the probe by one, two, three, or more nucleotides, although this is not preferred. Of course, the two primers may overlap with the probe target to different extents, or one may overlap and the other may not. Where the probe and the primer overlap, then the probe may compete with the primer for binding, preferably at the 3' end of the primer, and prevent extension in this way.

In preferred embodiments of the invention, the amplification reaction is polymerase chain reaction (PCR). In certain embodiments, the primers may be provided in different concentrations; preferably one of the primers is provided in a rate-limiting amount, and the amplification reaction is asymmetric PCR. In asymmetric PCR, one of the two target DNA strands is preferentially amplified, as the rate-limiting primer is used up so only the other primer is available to begin strand extension. Either the sense or the antisense strand may be the one targeted for preferential amplification; preferably the preferentially amplified strand is the complementary strand to the probe. In a particularly preferred embodiment, in which the primers are SEQ ID NO 2 and 3 referred to above, the asymmetric PCR is carried out with the excess primer being the reverse primer, at 12.5 pMol/20 µl reaction, the limiting primer being the forward primer at 1.5 pMol/20 µl reaction, and the probe at 3 pMol/20 µl reaction.

The present invention also provides an oligonucleotide probe comprising or consisting of the nucleotide sequence of SEQ ID NO 1. The probe is preferably DNA. The probe may further comprise one or more labels associated with the probe; preferably a fluorescent label associated with one or more nucleotides of the sequence. The labels may be selected so as to give a differential signal depending on whether the probe is in a double stranded duplex with a target sequence or is single stranded.

Also provided is a primer sequence selected to allow amplification of a target sequence recognised by the above-mentioned probes SEQ ID NO 1. The primer may consist of or comprise the nucleotide sequence of SEQ ID NO 2 or SEQ ID NO 3. In a preferred embodiment, the invention provides a primer pair with a first primer consisting of or comprising the nucleotide sequence of SEQ ID NO 2, and a second primer consisting of or comprising the nucleotide sequence of SEQ ID NO 3.

The invention may further provide a kit for detecting mutations in the JAK2 gene, the kit comprising a primer pair with a first primer consisting of or comprising the nucleotide sequence of SEQ ID NO 2, and a second primer consisting of or comprising the nucleotide sequence of SEQ ID NO 3; and a probe comprising or consisting of the nucleotide sequence of SEQ ID NO 1. The kit may optionally comprise instructions for use; and/or additional reagents necessary for carrying out nucleic acid amplification and/or detection.

BRIEF DESCRIPTION OF THE FIGURES

FIG. 1 gives the nucleotide sequence for the wild type JAK2 gene (SEQ ID NO 4)

FIG. 2 gives the primer and probe sequences of the present invention, as well as the amplicon details.

FIG. 5 lists the various mutations in the same region.

FIG. 6 gives example melt curves of wild type and mixed wild type-V617F samples from the current assay.

FIG. 7 shows thermal cycling steps used for analysis.

DETAILED DESCRIPTION OF THE INVENTION

The present invention provides a method whereby mutations in the JAK2 gene (for example, the V617F mutation) may be indirectly detected by detecting the presence or absence of the wild type sequence. The invention uses a single probe as both a blocker, to prevent amplification of the wild type allele, and a reporter, to report the presence of the wild type allele. Further, the probe can be used to detect multiple different alleles (for example, alternate SNPs) in the same locus from a single experiment. The method can be used to detect mutations such as SNPs as well as insertions or deletions.

The method as presented here makes use of hyBeacon® probes (which provide differential reporter signals depending on whether the probe is single stranded or double stranded) and asymmetric PCR (to preferentially amplify one strand of the target sequence). Typical sensitivity of the method is 1-5 copies of the mutant allele, and ratios greater than 5% SNP to wild type. A single assay using a single primer set and probe can detect multiple SNPs within the same probe sequence.

Example 1

JAK2

The sequence of the wild type JAK2 mRNA sequence (SEQ ID NO 4) is given in FIG. 1. Residue 2343 is highlighted.

FIG. 2 gives the sequences of forward and reverse primers, and the probe sequence for binding to wild type JAK2.

The V617F mutation in JAK2 results from a G2343T mutation in the nucleic acid sequence. The probe binds to the region spanning this mutation; if the mutation is present (or indeed any other mutation in that sequence), then the Tm of the hybridised probe is lowered.

As is apparent, the probe sequence is fully complementary to the relevant wild type target sequence, and has one mismatched base compared with each of the possible mutant sequences. The mismatch is internal to the probe, rather than at either of the ends. The probe is a hyBeacon® probe, having a pair of fluorophores which alter their emissions when the probe is in a double stranded duplex compared with single stranded form.

A sample of DNA containing the JAK2 region is amplified in a 20 µl total reaction volume using 12.5 pMol excess (forward) primer, 1.5 pMol limiting (reverse) primer, and 3 pMol probe. Cycling conditions are;

| | | |
|---|---|---|
| 95° C. | 5 minutes | Genomic DNA denaturation |
| 95° C. | 5 seconds | } 40x cycles |
| 53° C. | 5 seconds | |
| 72° C. | 5 seconds | |

End-point melt curve analysis at 45° C. to 75° C. at 0.1° C./sec

After amplification, the melt curve for the reaction product is analysed, to determine whether the wild type sequence is present.

Figure 3:
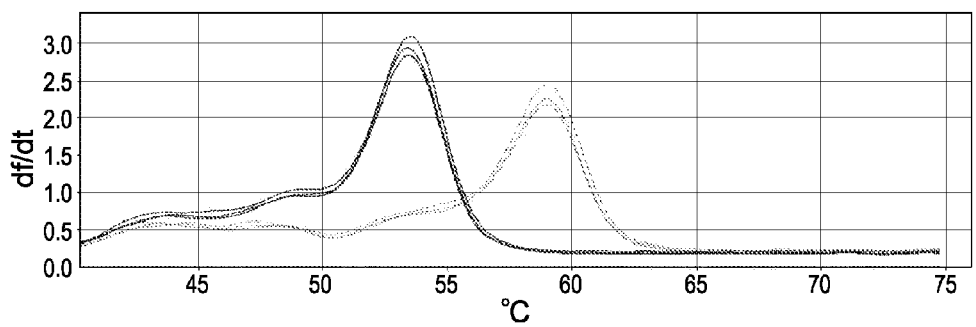
FIG. 3 shows the melt curve for the probe versus V617F mutant target (left hand curve, with a lower Tm) and versus the wild type target (right hand curve, with a higher Tm).

FIG. 3 shows the melt curve for the probe versus V617F mutant target (left hand curve, with a lower Tm) and versus the wild type target (right hand curve, with a higher Tm). It will be apparent that the two forms are clearly distinguishable, using a single probe. In the absence of the wild type product, a shifted melt curve will be obtained; this method allows for detection of any mutation within the probe region, and not only the V617F mutation.

Figure 4:
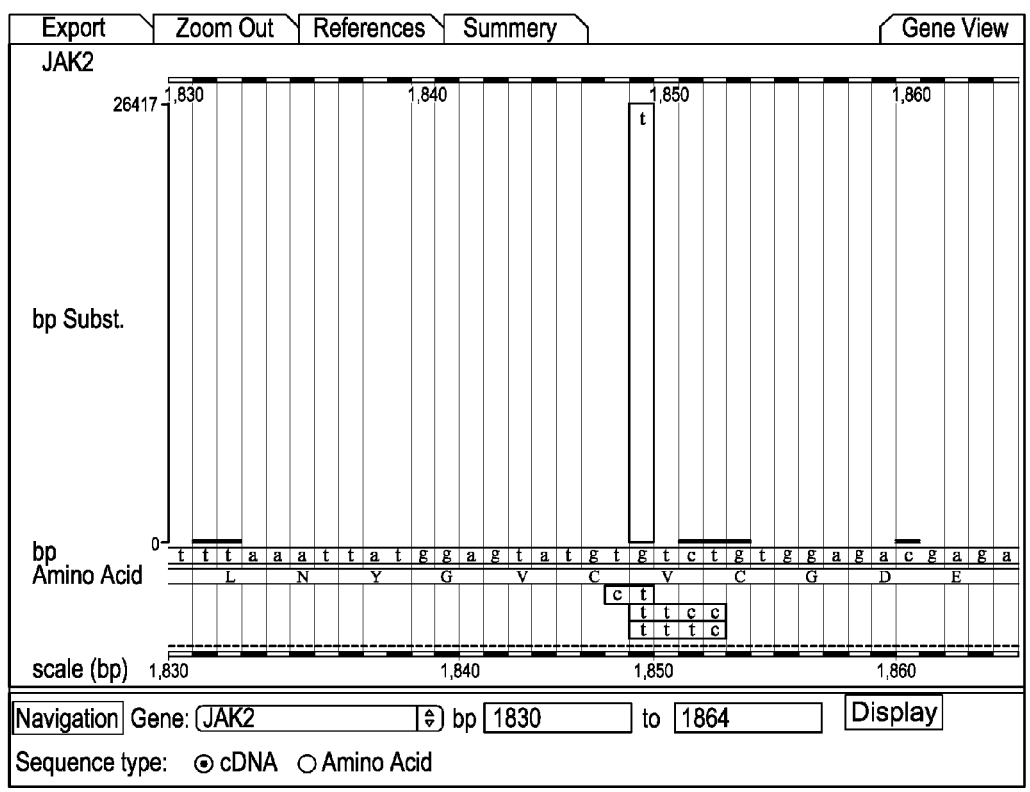
FIG. 4 shows the mutations which have been identified in the JAK2 gene in the region covered by the probe of SEQ ID NO 1.
Figure 8A:
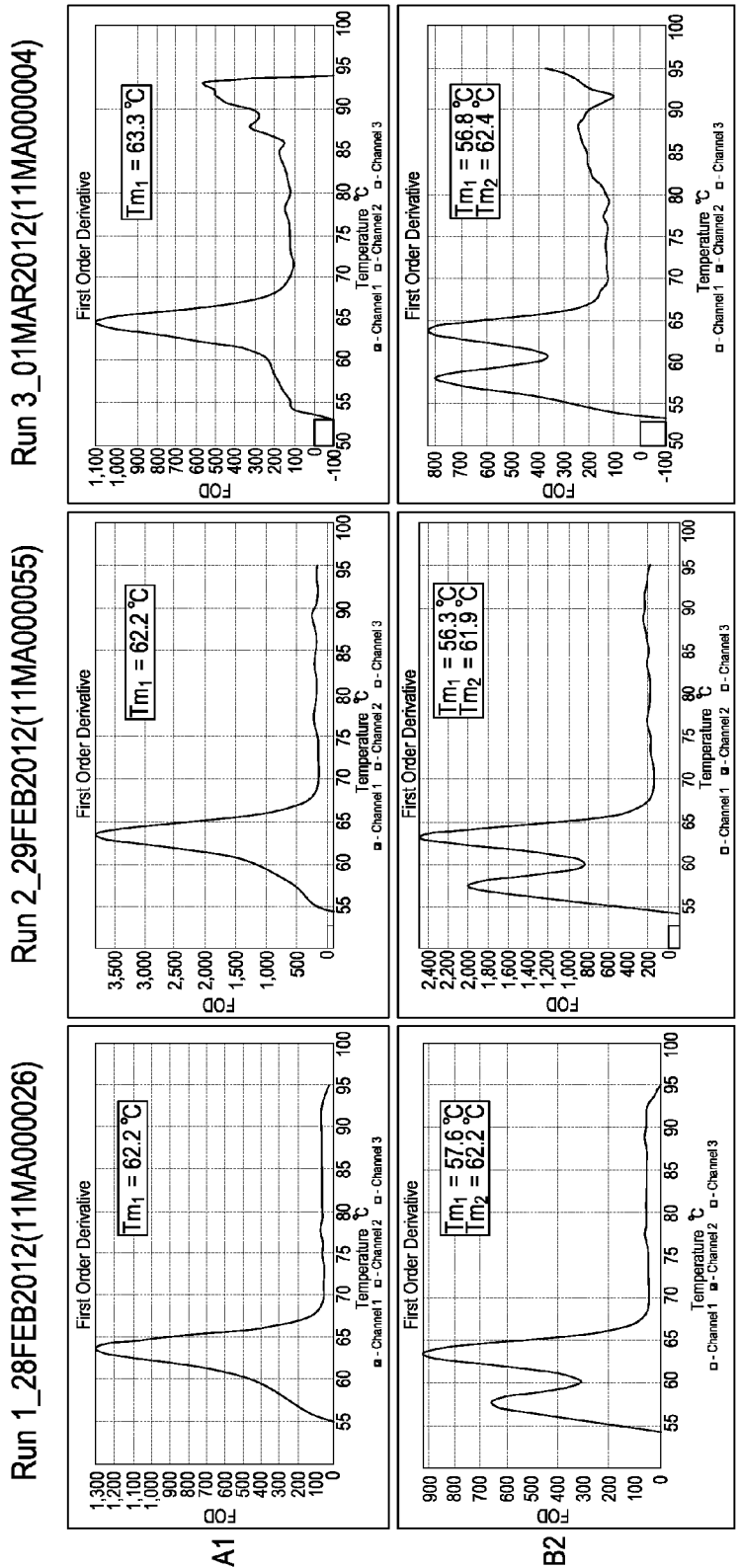
FIG. 8 shows thermal cycling steps used for Genedrive assay analysis with the LightCycler.
Figure 8A:
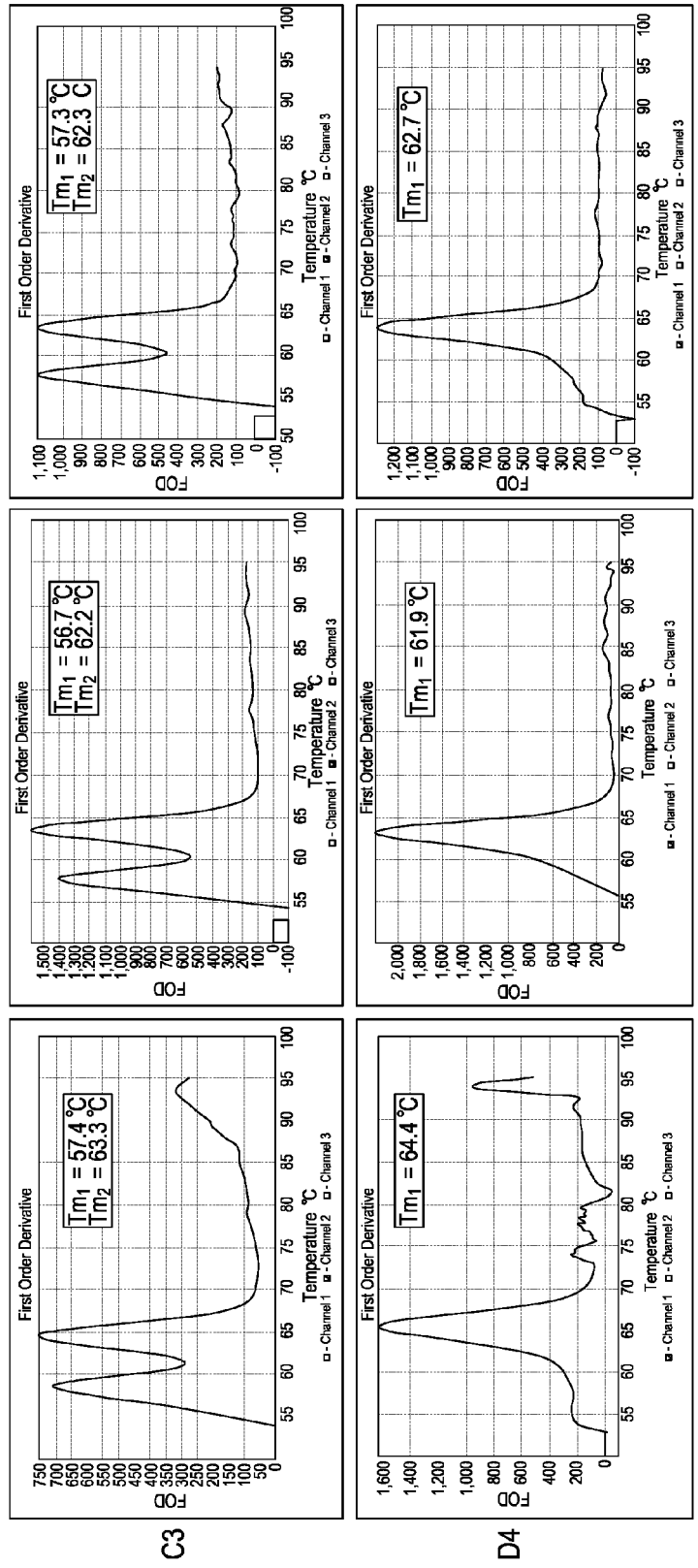
Figure 8B:
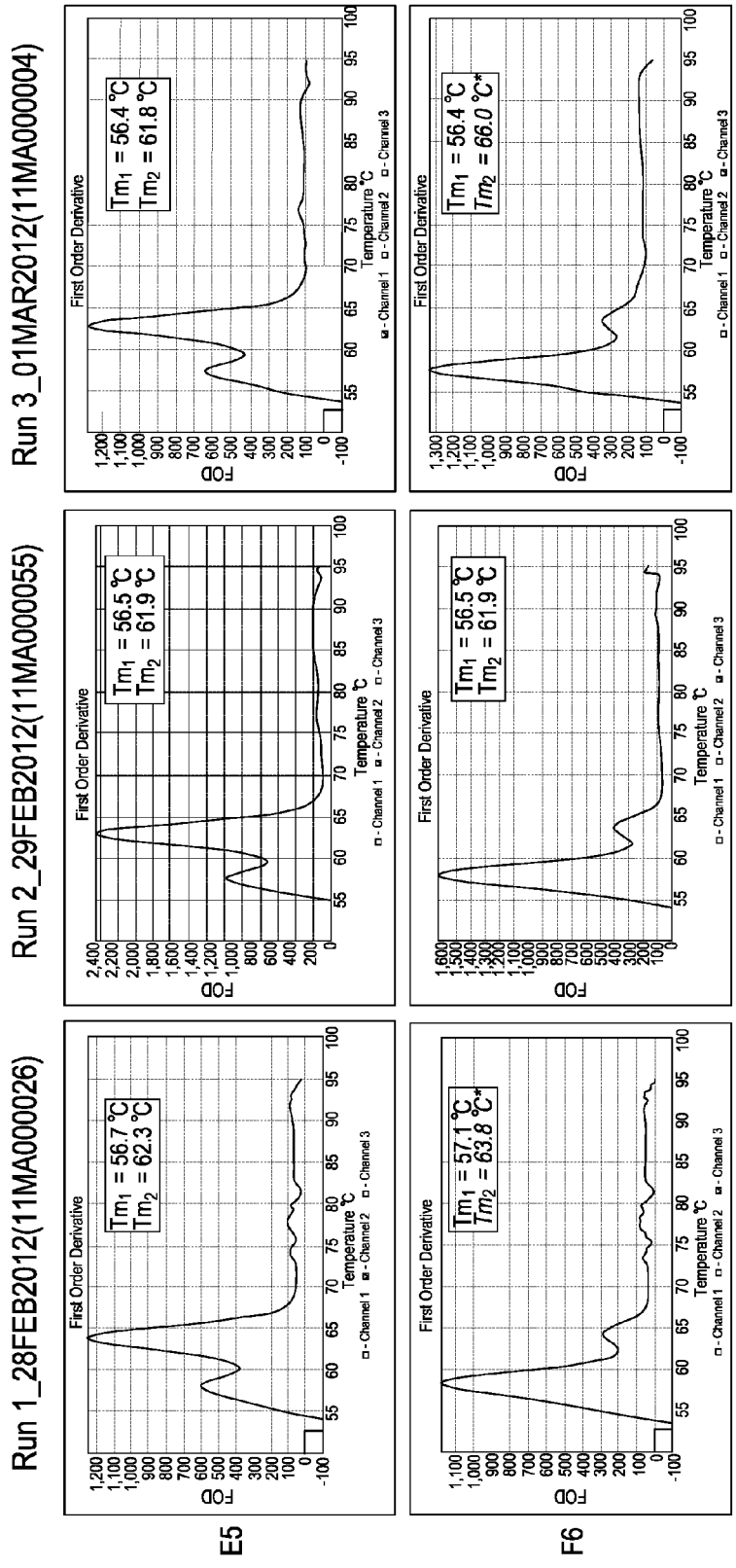
Figure 8B:
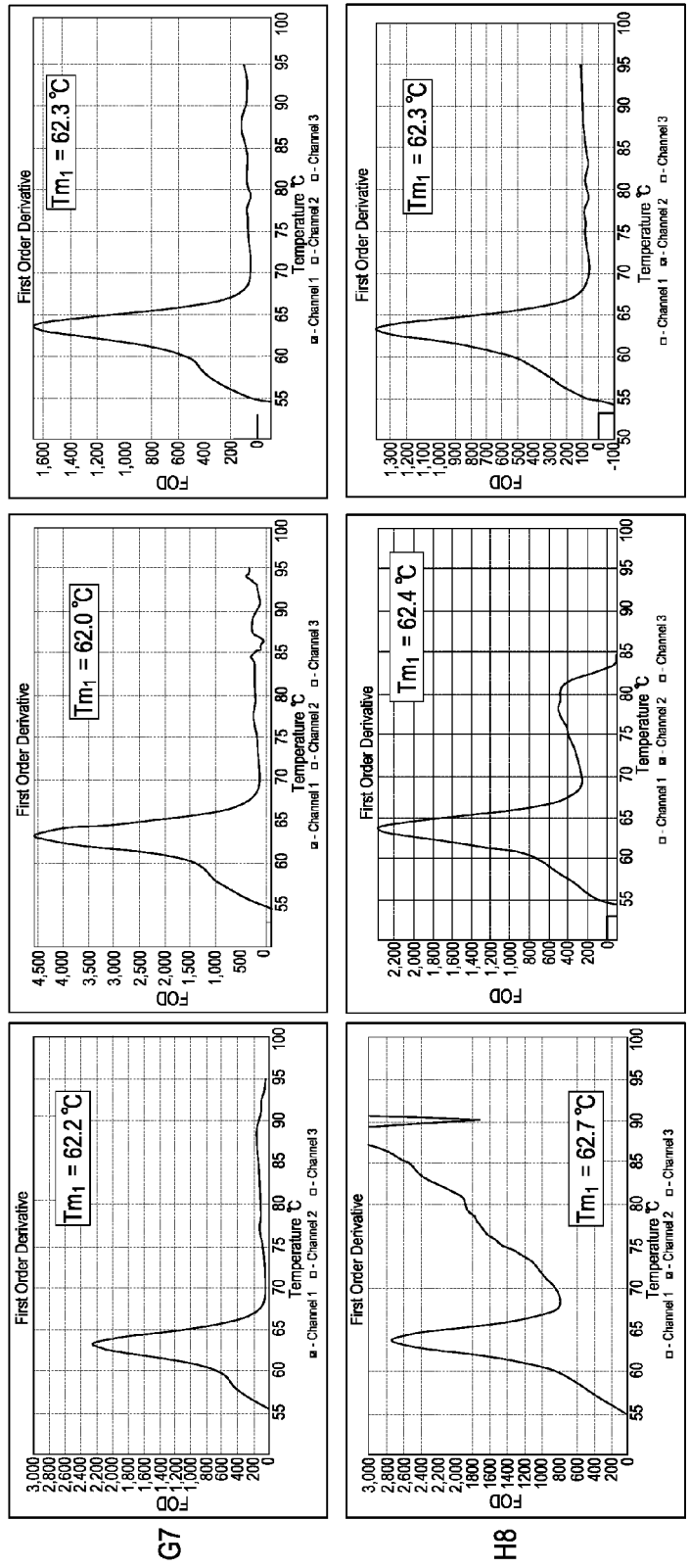
Figure 8C:
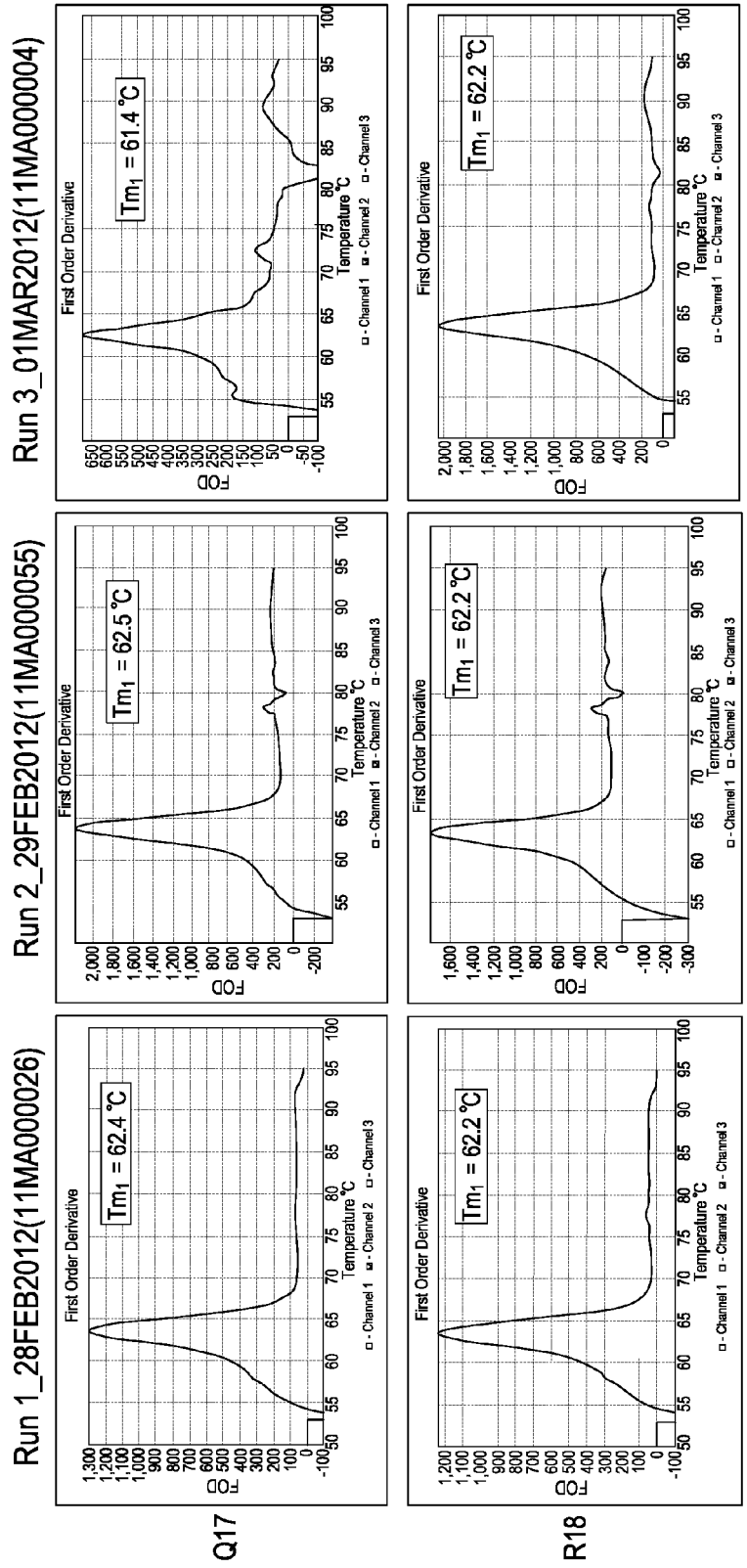
Figure 8C:
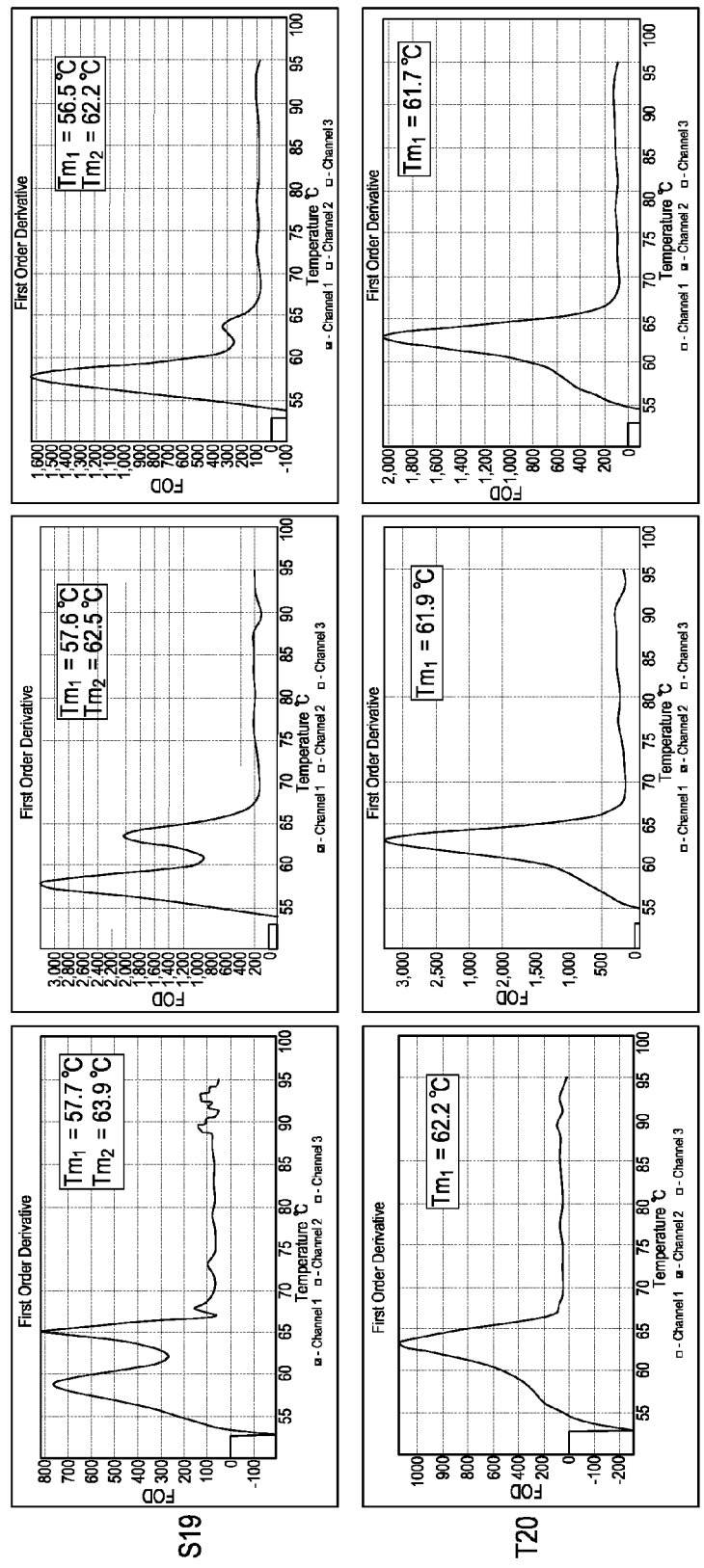
Figure 8D:
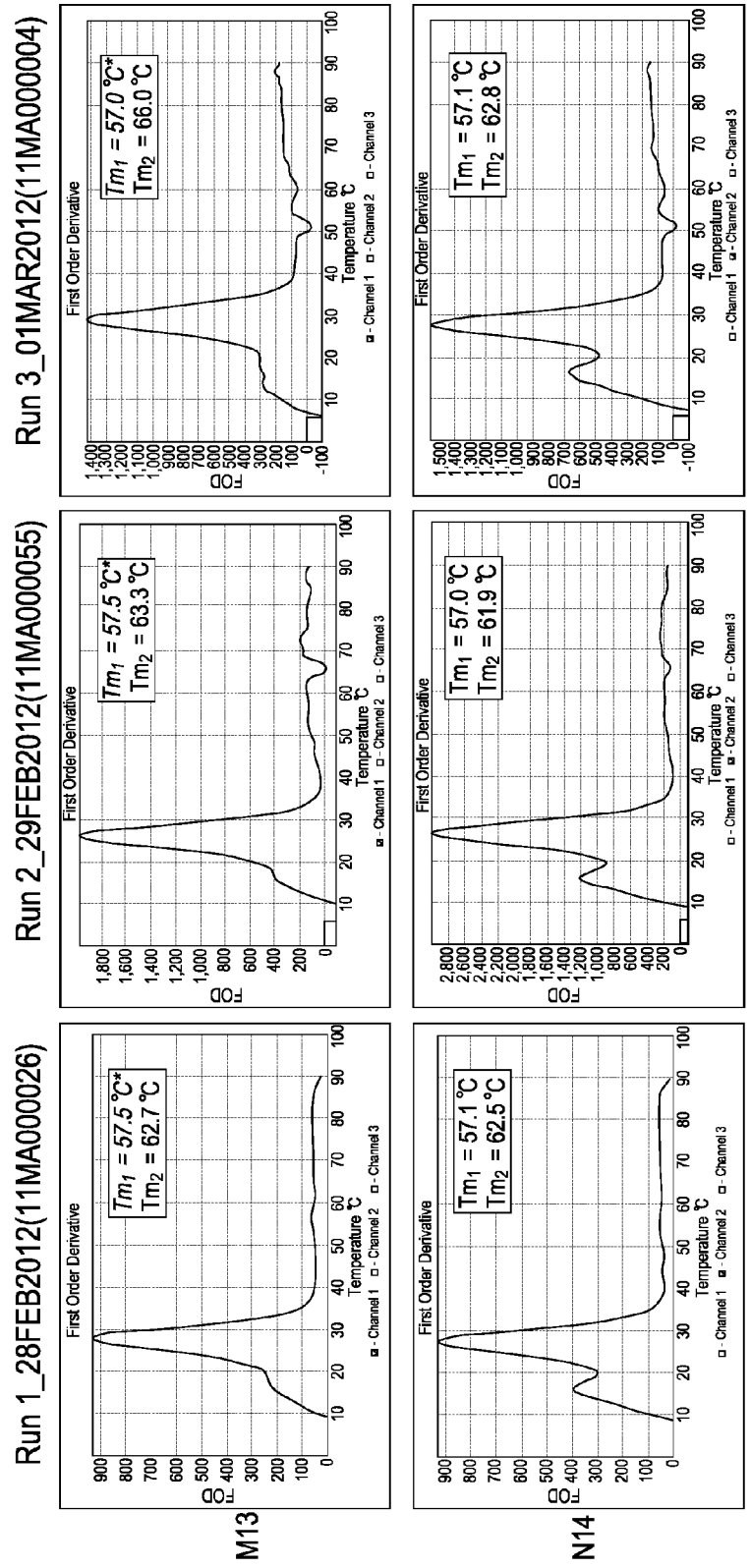
Figure 8D:
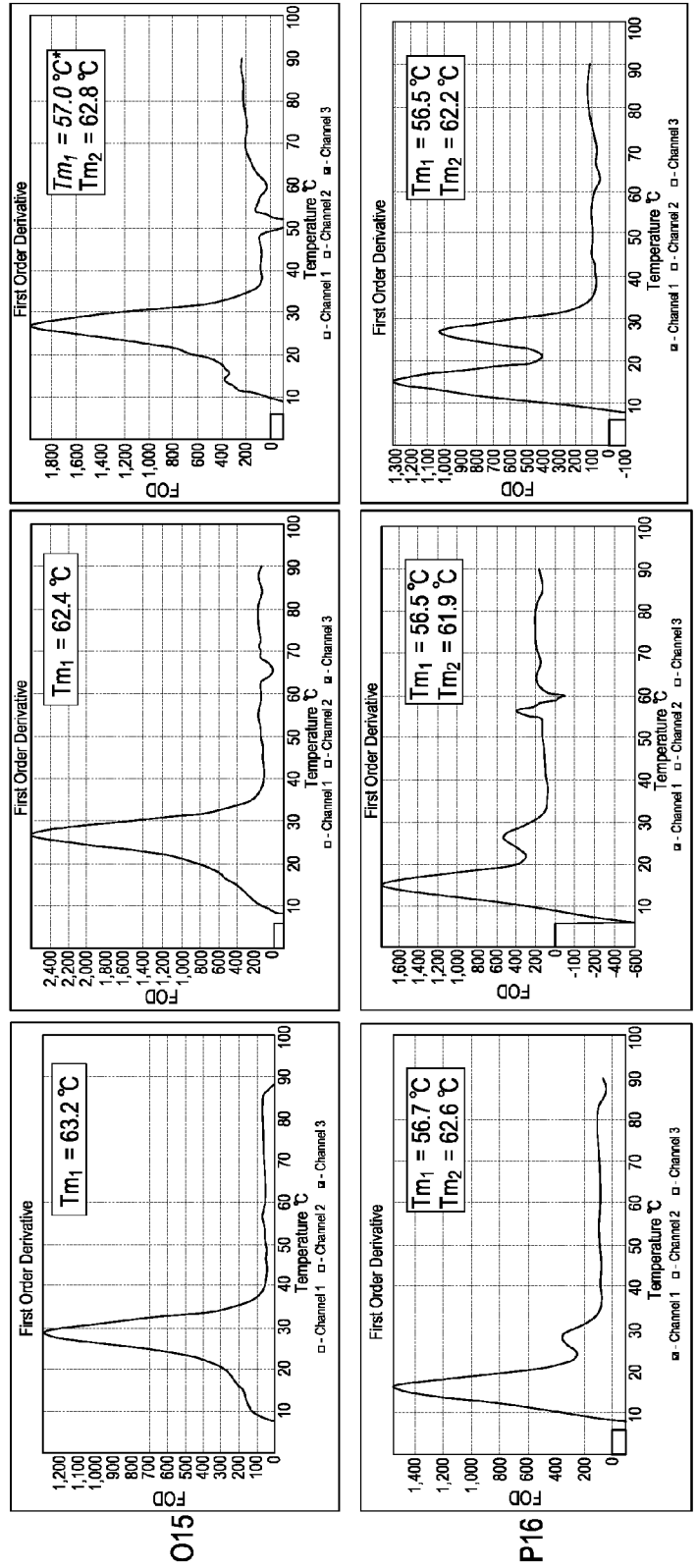
Figure 8E:
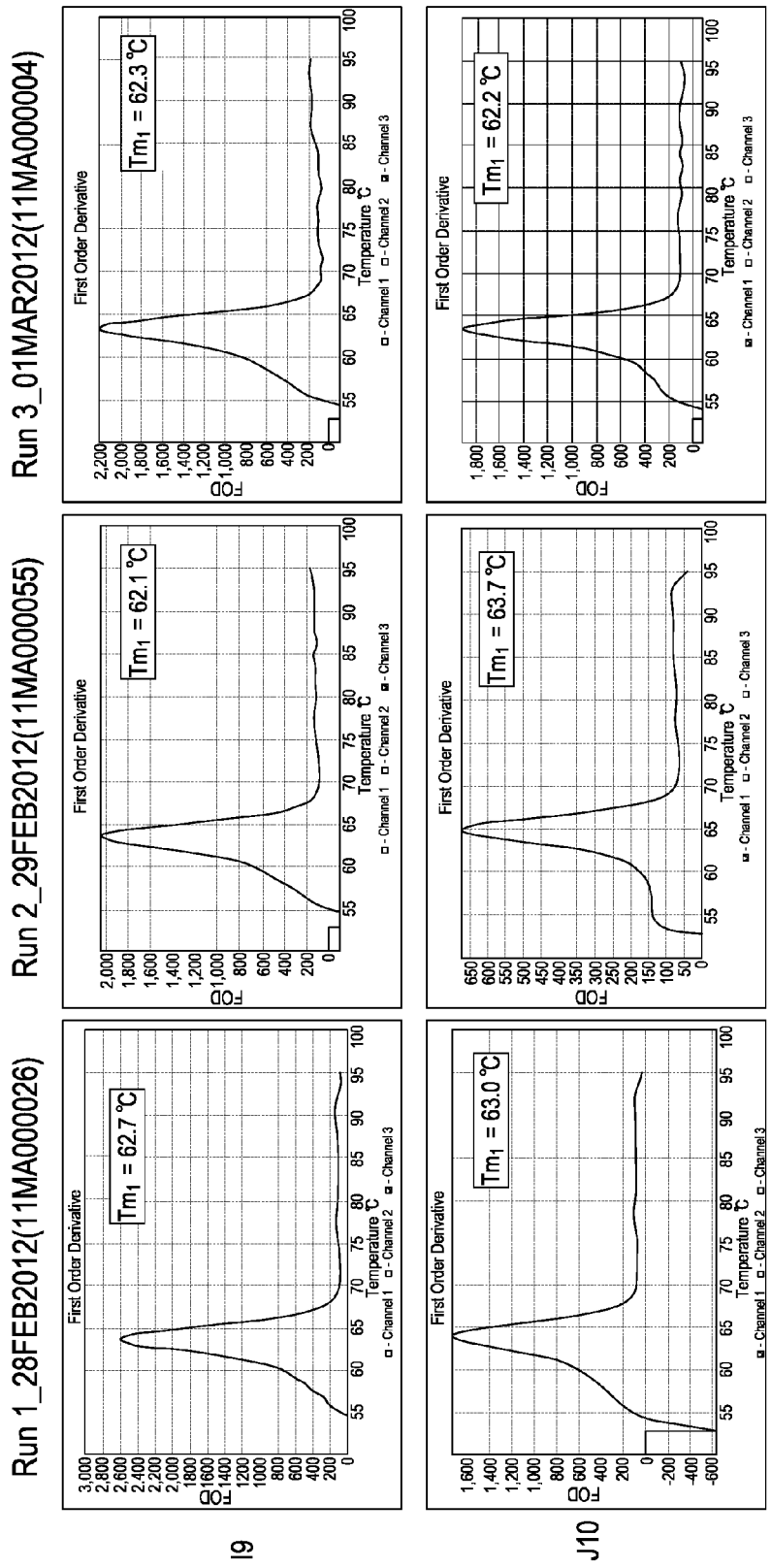
Figure 8E:
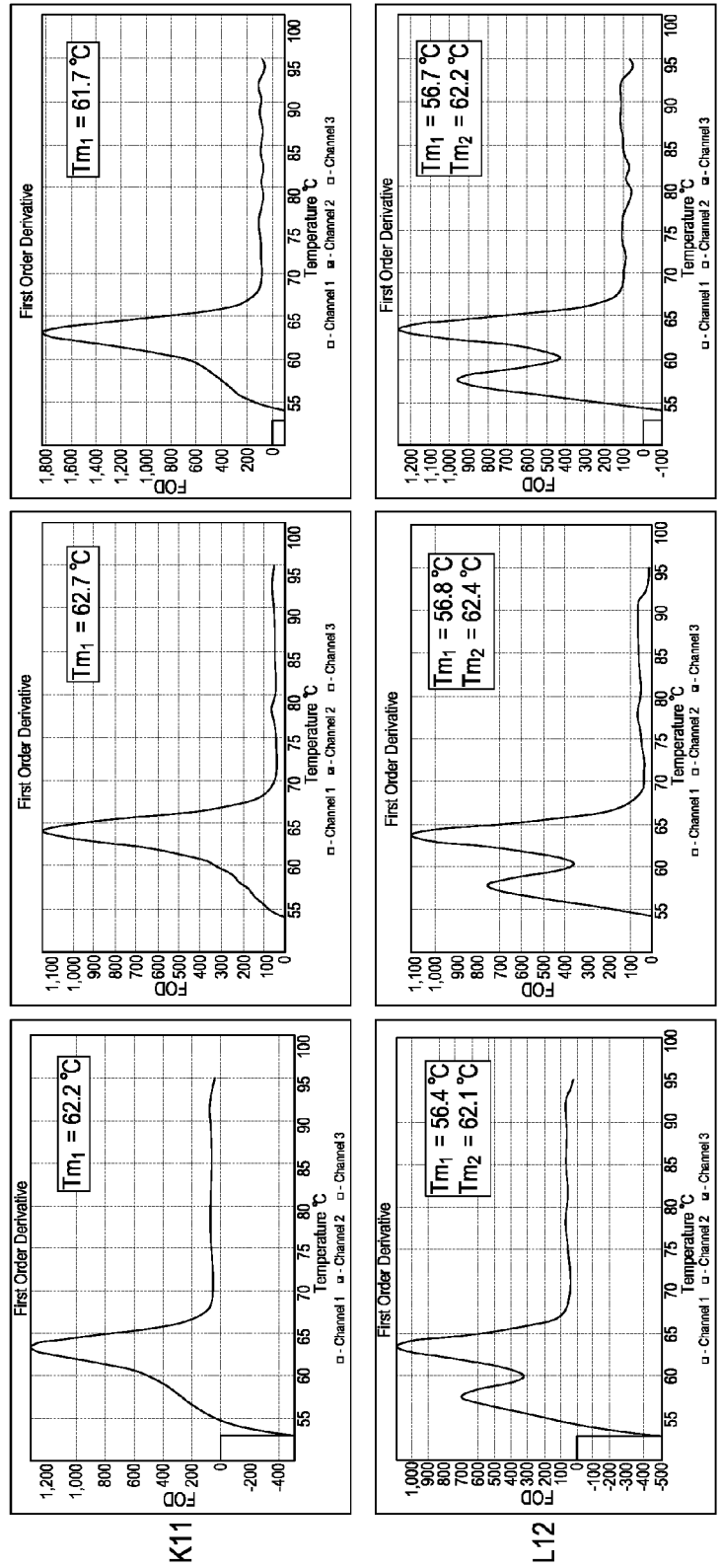

FIG. 4 shows the mutations which have been identified in the JAK2 gene in the region covered by the probe of SEQ ID NO 1. Note that the figure refers to nt 1830 to 1864; this corresponds to nt 2324 to 2358 of SEQ ID NO 4. FIG. 5 lists the various mutations in the same region. We believe that the present method is able to identify the presence of any of these mutations using the probe of SEQ ID NO 1.

The amplification methods described herein use asymmetric PCR, which preferentially amplifies one strand of the target DNA. Standard thermal cycling is carried out as in conventional PCR, but with a limiting amount of one primer (rate limited primer). When the limiting primer becomes depleted, replication increases arithmetically through extension of the excess primer.

Typically the probe is complementary to the non-primer-limited strand, so that the preferentially amplified strand may hybridise to the probe. The probe may then block amplification of that strand if hybridisation takes place—for example, if the sequence is that of the wild type rather than the mutant.

The skilled person will be able to design suitable alternative primers for use in the present method, to amplify a desired target sequence.

The probes used have a significantly higher melt temperature (Tm) when binding to the wild type than to the mutant. This allows use of the probe both as a blocker, to prevent amplification, and as a reporter, to report on the presence of the wild type or mutant sequence.

Using a hold/extension temperature set above the Tm of the probe:wild type duplex it is possible to preferentially bind the probe to the wild type without significant hybridisation to the mutant sequence. The anneal of the amplification primers is also chosen to be above the Tm of the probe:mutant duplex. The amplification primers bind to both wild type and mutant alleles, but amplification of the wild type is significantly reduced because of the blocking probe. This preferentially increases the population of mutant for subsequent rounds of amplification.

As an example, the first annealing step is at a high temperature (eg, 66.5 deg C.). In this blocking step, the probe binds to wild type and blocks forward primer hybridisation. There is no binding of the probe to the mutant, since Tm is too high. In the second annealing step, at a lower temperature (eg, 57 deg C.) the forward primer binds to the mutant in competition. There is little binding of the probe to the mutant since Tm is too high.

In the amplification reaction, the melt phase may take place at 95 deg C., then the temperature is lowered to 66.5 deg C. for the blocking anneal phase. It is then lowered further to 63 deg C. for the primer anneal and extension phases, before cycling back to 95 deg C. Thus, the mutant sequence is amplified, while the wild type is blocked. There may still be some amplification of the wild type sequence, but the mutant sequence is preferentially amplified, so increasing relative abundance in the sample.

Once the sample is amplified, the absence of wild type sequence may be determined by carrying out the melt curve analysis described. A benefit of using the hyBeacon® probes, or similar, is that the same single probe both blocks amplification of wild type to enrich amplification of mutant sequence, and reports both wild type:mutant ratio at the end of the assay. The method allows amplification of any mutant sequences within the probe region, and is completely independent of any SNP knowledge; i.e. can report unknown SNPs within the probe sequence. A single probe can enrich mutant SNPs on multiple codons within the single probe, and or multiple probes along a stretch. The technique can also be used to detect insertions/deletions, and is compatible with asymmetric amplification.

Example 2

Comparison With Other Tests

We conducted a comparison of the method described herein with other assays in order to determine reliability, accuracy, and sensitivity. Twenty blinded DNA samples for testing were obtained, and assayed using three different methodologies: 1. Genedrive assay (as described herein, using the Genedrive thermal cycling system from Epistem); 2. Genedrive assay using the Roche LightCycler 480 II; 3. JAK2 V617F MutaQuant kit (Ipsogen) on Roche LightCycler 480 II.

1. Genedrive Assay

Assay based on amplicon melt-curve analysis of WT and mutant peak heights. Blinded test samples analysed on Genedrive™, in singulate over three independent analytical runs on three different Genedrive™ units. V617F peak melting temperature (Tm)=56-58° C. JAK2 Wt peak Tm=61-65° C.

FIG. 6 shows example melt curves from wild type samples, and mixed wild type—V617F mutant samples.

FIG. 7 shows the thermal cycling steps used for analysis. Samples were run at 10 ng per reaction, 20 µl reaction per sample, and 40×PCR cycles. Melt curves for each sample run are shown in FIG. 8. Peak identification was performed by eye. Results are summarised in the table below.

| | GD | | | | | | | | |
|---|---|---|---|---|---|---|---|---|---|
| | run 1 Tm (° C.) | | run 2 Tm (° C.) | | run 3 Tm (° C.) | | mean Tm (° C.) | | |
| Sample ID | peak1 | peak2 | peak1 | peak2 | peak1 | peak2 | peak1 | peak2 | Call | BWH call |
| A1  | —    | 62.2 | —    | 62.2 | —    | 63.3 | —    | 62.6 | wt  | wt |
| B2  | 56.7 | 62.2 | 56.3 | 61.9 | 56.8 | 62.4 | 56.6 | 62.2 | mut | mut |
| C3  | 57.4 | 63.3 | 56.7 | 62.2 | 56.3 | 62.3 | 56.8 | 62.6 | mut | mut |
| D4  | —    | 64.4 | —    | 61.9 | —    | 62.7 | —    | 63.0 | wt  | Wt |
| E5  | 56.7 | 62.3 | 56.5 | 61.9 | 56.4 | 61.8 | 56.5 | 62.0 | mut | mut |
| F6  | 57.1 | 63.8 | 56.7 | 62.3 | 56.4 | 63.0 | 56.7 | 63.0 | mut | mut |
| G7  | —    | 62.2 | —    | 62.0 | —    | 62.3 | —    | 62.2 | wt  | mut (5.5%) |
| H8  | —    | 62.7 | —    | 62.4 | —    | 62.2 | —    | 62.4 | wt  | wt |
| I9  | —    | 62.7 | —    | 62.1 | —    | 62.3 | —    | 62.4 | wt  | wt |
| J10 | —    | 63.0 | —    | 63.7 | —    | 62.2 | —    | 63.0 | wt  | wt |
| K11 | —    | 62.2 | —    | 62.7 | —    | 61.7 | —    | 62.2 | wt  | mut (0.4%) |
| L12 | 56.4 | 62.1 | 56.8 | 62.4 | 56.7 | 62.2 | 56.6 | 62.2 | mut | mut |
| M13 | 57.5 | 62.7 | 57.5 | 61.8 | 57.0 | 63.3 | 57.3 | 62.6 | mut | mut |
| N14 | 57.1 | 62.5 | 57.0 | 61.9 | 57.1 | 62.8 | 57.1 | 62.4 | mut | mut |
| O15 | —    | 63.2 | —    | 62.4 | 57.0 | 62.3 | 57.0 | 62.6 | wt  | wt |
| P16 | 56.7 | 62.6 | 56.5 | 61.9 | 56.5 | 62.2 | 56.6 | 62.2 | mut | mut |
| Q17 | —    | 62.4 | —    | 62.5 | —    | 61.4 | —    | 62.1 | wt  | mut (2.2%) |
| R18 | —    | 62.2 | —    | 62.2 | —    | 62.2 | —    | 62.2 | wt  | mut (3.0%) |
| S19 | 57.7 | 63.9 | 56.6 | 62.5 | 56.5 | 62.2 | 56.9 | 61.9 | mut | mut |
| T20 | —    | 62.2 | —    | 61.9 | —    | 61.7 | —    | 61.9 | wt  | mut (1.2%) |

"Call" is the experimental determination of whether the sample is wild type or mutant.
"BWH call" is the determination of wild type or mutant from the unblinded sample.
15/20 sample calls are in agreement with BWH calls.
5/20 sample calls disagree with BWH calls (G7, K11, Q17, R18, T20).
Samples with differing calls contain ~5% or less V617F mutation burden suggesting this is the current limit of sensitivity of this assay.
The results are shown to be reproducible over 3 analytical runs.

2. Genedrive Assay/LightCycler Data

Again, samples were run at 10 ng per reaction, 20 μl reaction per sample, 40×PCR cycles. The cycle profile is shown in FIG. 8. The analysis method is melt curve genotyping and Tm calling; again, calls were made by eye to determine the presence of peaks. The raw data is not shown here, but the summary of results is given below:

| Sample ID | LightCycler assay Call | Genedrive ™ Call | BWH call |
|---|---|---|---|
| A1  | wt  | wt  | wt |
| B2  | mut | mut | mut |
| C3  | mut | mut | mut |
| D4  | wt  | wt  | wt |
| E5  | mut | mut | mut |
| F6  | mut | mut | mut |
| G7  | wt  | wt  | mut (5.5%) |
| H8  | wt  | wt  | wt |
| I9  | wt  | wt  | wt |
| J10 | wt  | wt  | wt |
| K11 | mut | wt  | mut (0.4%) |
| L12 | mut | mut | mut |
| M13 | mut | mut | mut |
| N14 | mut | mut | mut |
| O15 | wt  | wt  | wt |
| P16 | mut | mut | mut |
| Q17 | wt  | wt  | mut (2.2%) |
| R18 | wt  | wt  | mut (3.0%) |
| S19 | mut | mut | mut |
| T20 | wt  | wt  | mut (1.2%) |

16/20 sample calls in agreement with BWH calls (15/20 samples in agreement from Genedrive ™ data). 4/20 sample calls disagree with BWH calls (G7, Q17, R18, T20) compared to 5/20 calls disagreeing from Genedrive ™ data (G7, K11, Q17, R18, T20). Samples with differing calls contain ~5% or less V617F mutation burden suggesting this is the current limit of sensitivity of this assay. Sample K11 detected (0.4% V617F mutation) suggesting that detection of <5% V617F mutation may be variable.

3. Ipsogen JAK2 V617F MutaQuant Kit

Figure 9:
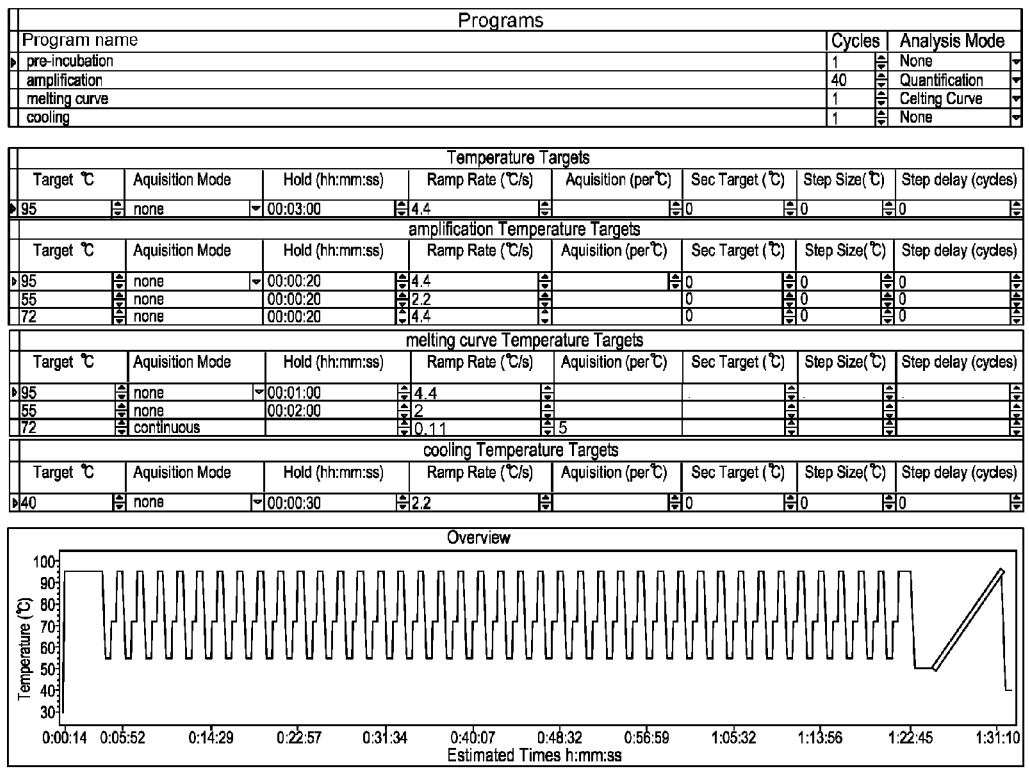
FIG. 9 shows thermal cycling steps used for Ipsogen JAK2 V617F MutaQuant kit analysis with the LightCycler.

JAK2 V617F MutaQuant kit (Ipsogen, cat# MQPP-02-CE, lot# 12-03-05) was used, together with TaqMan 2×PCR Master Mix (Applied Biosystems, cat# 4304437, lot# P07408). Standards, controls and master mixes prepared according to manufacturers instructions. Samples were run at 25 μl reaction per sample, 25 ng template DNA per reaction, 50× cycles. Cycling profile is shown in FIG. 9.

Figure 10:
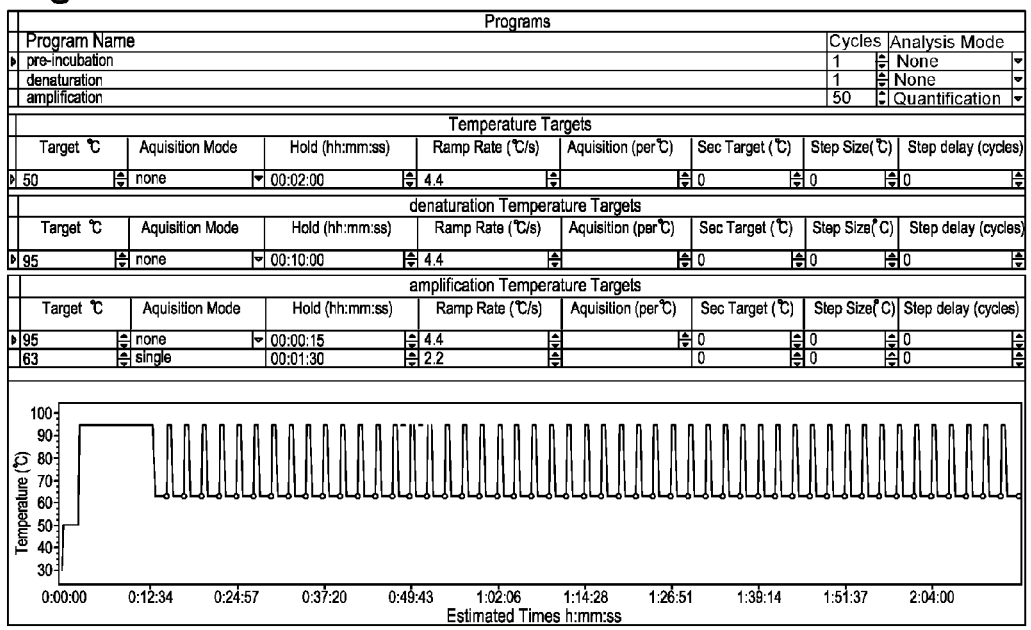
FIG. 10 shows illustrative results from the assay of FIG. 9 with known standards and controls.

17/20 BWH samples run to enable assay to be screened on a single 96-well plate (samples B2, D4 and E5 omitted). Data analysed using LightCycler® 480 Software release 1.5.0 (Roche Diagnostics, GmbH). Analysis method; Abs Quant/Fit points. Copy number calculated from standard curve generated from standard samples Illustrative results from known standards and controls are shown in FIG. 10. Summary results are shown below:

| Sample | V617F copy number | WTcopy number | Total copy number | JAK2 V617F % | Call | BWH call |
|---|---|---|---|---|---|---|
| A1 | 10.50    | 24650.00 | 24660.50 | 0.04  | wt  | wt |
| C3 | 18100.00 | 9300.00  | 27400.00 | 66.06 | mut | mut |
| F6 | 60650.00 | 5955.00  | 66605.00 | 91.06 | mut | mut |
| G7 | 4280.00  | 40650.00 | 44930.00 | 9.53  | mut | mut (5.5%) |
| H8 | 28.10    | 18610.00 | 18638.10 | 0.15  | wt  | wt |
| I9 | 9.46     | 51250.00 | 51259.46 | 0.02  | wt  | wt |
| J10 | 4.00    | 12830    | 12834.00 | 0.03  | wt  | wt |

-continued

| Sample | V617F copy number | WTcopy number | Total copy number | JAK2 V617F % | Call | BWH call |
|--------|-------------------|---------------|-------------------|--------------|------|----------|
| K11 | 172.50 | 7250.00 | 7422.50 | 2.32 | mut | mut (0.4%) |
| L12 | 12400.00 | 10160.00 | 22560.00 | 54.96 | mut | mut |
| M13 | 4585.00 | 27800.00 | 32385.00 | 14.16 | mut | mut |
| N14 | 16300.00 | 46500.00 | 62800.00 | 25.96 | mut | mut |
| O15 | 8.20 | 28150.00 | 28158.20 | 0.03 | wt | wt |
| P16 | 24700.00 | 1103.00 | 25803.00 | 95.73 | mut | mut |
| Q17 | 1255.00 | 21850.00 | 23105.00 | 5.43 | mut | mut (2.2%) |
| R18 | 686.50 | 13600.00 | 14286.50 | 4.81 | mut | mut (3.0%) |
| S19 | 34850.00 | 13350.00 | 48200.00 | 72.30 | mut | mut |
| T20 | 341.50 | 12130.00 | 12471.50 | 2.74 | mut | mut (1.2%) |

The results of Ipsogen MutaQuant screen were in agreement with BWH results for all samples screened. Although this is superficially a better outcome, the Genedrive assays used 40 cycle PCR programs, rather than 50 as was the case with the Ipsogen assay, and a lower starting amount of template (10 ng vs 25 ng). It is possible that increasing the starting template and the number of cycles would improve the sensitivity of the Genedrive assay. Nonetheless, it is clear that the Genedrive method described herein is of comparable sensitivity and accuracy to existing methods, and provides an alternative assay for JAK2 mutations. Further, the method has the advantage that it is not necessary to know which specific mutation will be present in advance, and can operate with smaller sample amounts and fewer amplification cycles.

The invention claimed is:

1. A method of detecting the absence of a wild type allele of a locus in the JAK2 gene having at least first mutant and wild type alleles, the method comprising:
   a) providing a reaction mix comprising
      i) a sample including nucleic acid representing at least a portion of the JAK2 gene;
      ii) an oligonucleotide probe which hybridises to the mutant allele with a lower melting temperature (Tm) than that with which it hybridises to the wild type allele;
      iii) a pair of oligonucleotide primers for nucleic acid amplification, the primers hybridising to the nucleic acid in the sample at first and second sites flanking the oligonucleotide probe binding site; wherein the Tm of the primer:sample is higher than the Tm of the probe:mutant allele;
   b) maintaining the reaction mix at a temperature between the probe:mutant allele Tm and the probe:wild type allele Tm, such that the probe preferentially hybridises to the wild type allele;
   c) carrying out a thermal cycling amplification on the reaction mix, the amplification including a melt phase, an annealing phase, and an extension phase, in which the temperatures of the extension and annealing phases are between the probe:mutant allele Tm and the probe:wild type allele Tm, such that the probe is hybridised to the wild type allele during these phases; to thereby amplify the mutant allele; and
   d) detecting hybridisation of the probe to the sample at a temperature at or below the probe:mutant allele Tm; detecting hybridisation of the probe to the sample at a higher temperature at or below the probe:wild type allele Tm; and comparing the two; to thereby detect the absence of the wild type allele, wherein if there is hybridisation of the probe to the sample at a temperature at or below the probe:mutant allele Tm and higher than the probe:wild-type allele Tm but not at a temperature higher than the probe:mutant allele Tm, then the wild type allele is absent; and
   wherein one or both of the primers has a binding site such that the probe competes with the primer for binding, to thereby prevent binding of the primer and hence strand extension.

2. The method of claim 1 wherein the portion of the JAK2 gene represented by the sample in step a)i) spans nt 2343 of the JAK2 gene as given by SEQ ID NO 4.

3. The method of claim 2 wherein the mutant allele is a mutation in nt2343.

4. The method of claim 3 wherein the mutant form is T2343, while the wild type is G2343.

5. The method of claim 2 wherein the probe is designed to span nt 2343 and sufficient additional nucleotides to be able to detect mutations in amino acid residue 618.

6. The method of claim 2 wherein the probe spans nt 2343.

7. The method of claim 1 wherein the oligonucleotide probe is at least 15 nucleotides in length.

8. The method of claim 1 wherein the oligonucleotide probe consists of the sequence TTT AAA TTA TGG AGT ATG TGT CTG TGG AGA (SEQ ID NO: 1).

9. The method of claim 1 wherein the primers amplify a portion of the JAK2 sequence which is at least 50 nucleotides in length.

10. The method of claim 1 wherein at least one of the primers consists of the nucleotide sequence TCT TTG AAG CAG CAA GTA TGA TGA (SEQ ID NO 2; sense primer) or GCA TTA GAA AGC CTG TAG TTT TAC TT (SEQ ID NO 3, antisense primer).

11. The method of claim 10 wherein the primers consist of the nucleotide sequence TCT TTG AAG CAG CAA GTA TGA TGA (SEQ ID NO 2; sense primer) and GCA TTA GAA AGC CTG TAG TTT TAC TT (SEQ ID NO 3, antisense primer).

12. The method of claim 1 wherein the probe is labelled.

13. The method of claim 12 wherein the label generates a differential signal depending on whether the probe has hybridised to a target strand or has not hybridised to a target strand.

* * * * *

SEQUENCE LISTING

```
<160> NUMBER OF SEQ ID NOS: 4

<210> SEQ ID NO 1
<211> LENGTH: 30
<212> TYPE: DNA
<213> ORGANISM: artificial
<220> FEATURE:
<223> OTHER INFORMATION: oligonucleotide probe corresponding to nt 2324
      to 2353 of JAK2

<400> SEQUENCE: 1
tttaaattat ggagtatgtg tctgtggaga                                         30

<210> SEQ ID NO 2
<211> LENGTH: 24
<212> TYPE: DNA
<213> ORGANISM: artificial
<220> FEATURE:
<223> OTHER INFORMATION: sense primer for JAK2

<400> SEQUENCE: 2
tctttgaagc agcaagtatg atga                                               24

<210> SEQ ID NO 3
<211> LENGTH: 26
<212> TYPE: DNA
<213> ORGANISM: artificial
<220> FEATURE:
<223> OTHER INFORMATION: antisense primer for JAK2

<400> SEQUENCE: 3
gcattagaaa gcctgtagtt ttactt                                             26

<210> SEQ ID NO 4
<211> LENGTH: 5285
<212> TYPE: DNA
<213> ORGANISM: Homo sapiens

<400> SEQUENCE: 4
ctgcaggaag gagagaggaa gaggagcaga aggggggcagc agcggacgcc gctaacggcc        60
tccctcggcg ctgacaggct gggccggcgc ccggctcgct tgggtgttcg cgtcgccact       120
```

```
tcggcttctc ggccggtcgg gcccctcggc ccgggcttgc ggcgcgcgtc ggggctgagg      180
gctgctgcgg cgcagggaga ggcctggtcc tcgctgccga gggatgtgag tgggagctga      240
gcccacactg gagggccccc gagggcccag cctggaggtc gttcagagcc gtgcccgtcc      300
cggggcttcg cagaccttga cccgccgggt aggagccgcc cctgcgggct cgagggcgcg      360
ctctggtcgc ccgatctgtg tagccggttt cagaagcagg caacaggaac aagatgtgaa      420
ctgtttctct tctgcagaaa aagaggctct tcctcctcct cccgcgacgg caaatgttct      480
gaaaaagact ctgcatggga atggcctgcc ttacgatgac agaaatggag ggaacatcca      540
cctcttctat atatcagaat ggtgatattt ctggaaatgc caattctatg aagcaaatag      600
atccagttct tcaggtgtat ctttaccatt cccttgggaa atctgaggca gattatctga      660
cctttccatc tggggagtat gttgcagaag aaatctgtat tgctgcttct aaagcttgtg      720
gtatcacacc tgtgtatcat aatatgtttg ctttaatgag tgaaacagaa aggatctggt      780
atccacccaa ccatgtcttc catatagatg agtcaaccag gcataatgta ctctacagaa      840
taagatttta ctttcctcgt tggtattgca gtggcagcaa cagagcctat cggcatggaa      900
tatctcgagg tgctgaagct cctcttcttg atgactttgt catgtcttac ctctttgctc      960
agtggcggca tgattttgtg cacgatggaa taaaagtacc tgtgactcat gaaacacagg     1020
aagaatgtct tgggatggca gtgttagata tgatgagaat agccaaagaa acgatcaaa      1080 cccccactggc catctataac tctatcagct acaagacatt cttaccaaaa tgtattcgag     1140
caaagatcca agactatcat attttgacaa ggaagcgaat aaggtacaga tttcgcagat     1200
ttattcagca attcagccaa tgcaaagcca ctgccagaaa cttgaaactt aagtatctta     1260
taaatctgga aactctgcag tctgccttct acacagagaa atttgaagta aaagaacctg     1320
gaagtggtcc ttcaggtgag gagattttg caaccattat aataactgga aacggtggaa     1380
ttcagtggtc aagagggaaa cataaagaaa gtgagacact gacagaacag gatttacagt     1440
tatattgcga ttttcctaat attattgatg tcagtattaa gcaagcaaac caagagggtt     1500
caaatgaaag ccgagttgta actatccata gcaagatgg taaaaatctg gaaattgaac      1560
ttagctcatt aagggaagct ttgtctttcg tgtcattaat tgatggatat tatagattaa     1620
ctgcagatgc acatcattac ctctgtaaag aagtagcacc tccagccgtg cttgaaaata     1680
tacaaagcaa ctgtcatggc ccaatttcga tggattttgc cattagtaaa ctgaagaaag     1740
caggtaatca gactggactg tatgtacttc gatgcagtcc taaggacttt aataaatatt     1800
ttttgacttt tgctgtcgag cgagaaaatg tcattgaata taaacactgt ttgattacaa     1860
aaaatgagaa tgaagagtac aacctcagtg ggacaaagaa gaacttcagc agtcttaaag     1920
atcttttgaa ttgttaccag atggaaactg ttcgctcaga caatataatt ttccagttta     1980
ctaaatgctg tccccaaag ccaaaagata aatcaaacct tctagtcttc agaacgaatg      2040
gtgtttctga tgtaccaacc tcaccaacat tacagaggcc tactcatatg aaccaaatgg     2100
tgtttcacaa aatcagaaat gaagatttga tatttaatga aagccttggc caaggcactt     2160
ttacaaagat ttttaaaggc gtacgaagag aagtaggaga ctacggtcaa ctgcatgaaa     2220
cagaagttct tttaaaagtt ctggataaag cacacagaaa ctattcagag tctttctttg     2280
aagcagcaag tatgatgagc aagctttctc acaagcattt ggttttaaat tatggagtat     2340
gtgtctgtgg agacgagaat attctggttc aggagtttgt aaaatttgga tcactagata     2400
catatctgaa aaagaataaa aattgtataa atatattatg gaaacttgaa gttgctaaac     2460
agttggcatg ggccatgcat tttctagaag aaaacaccct tattcatggg aatgtatgtg     2520
```

```
ccaaaaatat tctgcttatc agagaagaag acaggaagac aggaaatcct cctttcatca      2580
aacttagtga tcctggcatt agtattacag ttttgccaaa ggacattctt caggagagaa      2640
taccatgggt accacctgaa tgcattgaaa atcctaaaaa tttaaatttg gcaacagaca      2700
aatggagttt tggtaccact ttgtgggaaa tctgcagtgg aggagataaa cctctaagtg      2760
ctctggattc tcaaagaaag ctacaatttt atgaagatag gcatcagctt cctgcaccaa      2820
agtgggcaga attagcaaac cttataaata attgtatgga ttatgaacca gatttcaggc      2880
cttctttcag agccatcata cgagatctta acagtttgtt tactccagat tatgaactat      2940
taacagaaaa tgcatgttta ccaaatatga ggataggtgc cctggggttt tctggtgcct      3000
ttgaagaccg ggatcctaca cagtttgaag agagacattt gaaatttcta cagcaacttg      3060
gcaagggtaa ttttgggagt gtggagatgt gccggtatga ccctctacag gacaacactg      3120
gggaggtggt cgctgtaaaa aagcttcagc atagtactga agagcaccta agagactttg      3180
aaagggaaat tgaaatcctg aaatccctac agcatgacaa cattgtaaag tacaagggag      3240
tgtgctacag tgctggtcgg cgtaatctaa aattaattat ggaatattta ccatatggaa      3300
gtttacgaga ctatcttcaa aaacataaag aacggataga tcacataaaa cttctgcagt      3360
acacatctca gatatgcaag ggtatggagt atcttggtac aaaaaggtat atccacaggg      3420
atctggcaac gagaaatata ttggtggaga acgagaacag agttaaaatt ggagattttg      3480
ggttaaccaa agtcttgcca caagacaaag aatactataa agtaaaagaa cctggtgaaa      3540
gtcccatatt ctggtatgct ccagaatcac tgacagagag caagttttct gtggcctcag      3600
atgtttggag ctttggagtg ttctgtatg aacttttcac atacattgag aagagtaaaa      3660
gtccaccagc ggaatttatg cgtatgattg gcaatgacaa acaaggacag atgatcgtgt      3720
tccatttgat agaactttg aagaataatg gaagattacc aagaccagat ggatgcccag      3780
atgagatcta tatgatcatg acagaatgct ggaacaataa tgtaaatcaa cgcccctcct      3840
ttagggatct agctcttcga gtggatcaaa taagggataa catggctgga tgaaagaaat      3900
gaccttcatt ctgagaccaa agtagattta cagaacaaag ttttatattt cacattgctg      3960
tggactatta ttacatatat cattattata taaatcatga tgctagccag caaagatgtg      4020
aaaatatctg ctcaaaactt tcaaagttta gtaagttttt cttcatgagg ccaccagtaa      4080
aagacattaa tgagaattcc ttagcaagga ttttgtaaga agtttcttaa acattgtcag      4140
ttaacatcac tcttgtctgg caaaagaaaa aaaatagact ttttcaactc agcttttga      4200 gacctgaaaa aattattatg taaattttgc aatgttaaag atgcacagaa tatgtatgta      4260
tagtttttac cacagtggat gtataatacc ttggcatctt gtgtgatgtt ttacacacat      4320
gagggctggt gttcattaat actgtttct aattttccca tagttaatct ataattaatt      4380
acttcactat acaaacaaat taagatgttc agataattga ataagtaccct ttgtgtcctt      4440 gttcatttat atcgctggcc agcattataa gcaggtgtat acttttagct tgtagttcca      4500
tgtactgtaa atattttca cataaaggga acaaatgtct agttttattt gtataggaaa      4560
tttccctgac cctaaataat acatttgaa atgaaacaag cttacaaaga tataatctat      4620
tttattatgg tttcccttgt atctatttgt ggtgaatgtg ttttttaaat ggaactatct      4680
ccaaattttt ctaagactac tatgaacagt tttctttaa aattttgaga ttaagaatgc      4740
caggaatatt gtcatcctt gagctgctga ctgccaataa cattcttcga tctctgggat      4800
ttatgctcat gaactaaatt taagcttaag ccataaaata gattagattg ttttttaaaa      4860
```

| | | | | | | |
|---|---|---|---|---|---|---|
| atggatagct | cattaagaag | tgcagcaggt | taagaatttt | ttcctaaaga | ctgtatattt | 4920 |
| gaggggtttc | agaattttgc | attgcagtca | tagaagagat | ttatttcctt | tttagagggg | 4980 |
| aaatgaggta | aataagtaaa | aaagtatgct | tgttaatttt | attcaagaat | gccagtagaa | 5040 |
| aattcataac | gtgtatcttt | aagaaaaatg | agcatacatc | ttaaatcttt | tcaattaagt | 5100 |
| ataagggggtt | gttcgttgtt | gtcatttgtt | atagtgctac | tccactttag | acaccatagc | 5160 |
| taaaataaaa | tatggtgggt | tttgtgtgtg | tgtgtgtgtg | tgtgtgtgtg | tgtgtgtgtg | 5220 |
| tgttatttat | acaaaactta | aaatacttgc | tgttttgatt | aaaaagaaaa | tagtttctta | 5280 |
| cttta | | | | | | 5285 |